US011191805B2

(12) United States Patent
Watnick

(10) Patent No.: US 11,191,805 B2
(45) Date of Patent: Dec. 7, 2021

(54) CYCLIC PROSAPOSIN PEPTIDES AND USES THEREOF

(71) Applicant: CHILDREN'S MEDICAL CENTER CORPORATION, Boston, MA (US)

(72) Inventor: Randolph S. Watnick, Newton, MA (US)

(73) Assignee: CHILDREN'S MEDICAL CENTER CORPORATION, Boston, MA (US)

( * ) Notice: Subject to any disclaimer, the term of this patent is extended or adjusted under 35 U.S.C. 154(b) by 0 days.

(21) Appl. No.: 16/854,792

(22) Filed: Apr. 21, 2020

(65) Prior Publication Data

US 2020/0246419 A1    Aug. 6, 2020

Related U.S. Application Data

(62) Division of application No. 15/128,617, filed as application No. PCT/US2015/022745 on Mar. 26, 2015, now Pat. No. 10,646,541.

(60) Provisional application No. 61/970,853, filed on Mar. 26, 2014.

(51) Int. Cl.
*A61K 38/12* (2006.01)
*C07K 7/64* (2006.01)
*A61K 38/08* (2019.01)

(52) U.S. Cl.
CPC .............. *A61K 38/12* (2013.01); *A61K 38/08* (2013.01); *C07K 7/64* (2013.01)

(58) Field of Classification Search
None
See application file for complete search history.

(56) References Cited

U.S. PATENT DOCUMENTS

| 5,565,332 | A | 10/1996 | Hoogenboom et al. |
| 5,696,080 | A | 12/1997 | O'Brien et al. |
| 5,700,909 | A | 12/1997 | O'Brien |
| 5,714,459 | A | 2/1998 | O'Brien et al. |
| 5,817,752 | A | 10/1998 | Yu |
| 6,500,431 | B1 | 12/2002 | Gill |
| 6,590,074 | B1 | 7/2003 | O'Brien et al. |
| 6,638,911 | B1 | 10/2003 | Blaschuk |
| 7,166,691 | B2 | 1/2007 | Koochekpour et al. |
| 7,341,730 | B1 | 3/2008 | Gill |
| 10,267,799 | B2 | 4/2019 | Watnick |
| 2002/0177551 | A1 | 11/2002 | Terman |
| 2004/0120961 | A1 | 6/2004 | Koochekpour et al. |
| 2004/0219609 | A1 | 11/2004 | Day et al. |
| 2004/0229799 | A1 | 11/2004 | Qi |
| 2006/0275274 | A1 | 12/2006 | Onichtchouk et al. |
| 2007/0099251 | A1 | 5/2007 | Zhang et al. |
| 2009/0269373 | A1 | 10/2009 | Qi |
| 2010/0144603 | A1 | 6/2010 | Watnick |
| 2013/0072425 | A1 | 3/2013 | Watnick |

FOREIGN PATENT DOCUMENTS

| WO | WO-95/03821 | 2/1995 |
| WO | WO-99/12559 | 3/1999 |
| WO | WO-00/02902 | 1/2000 |
| WO | WO-02/24952 | 3/2002 |
| WO | WO-2004/084930 | 10/2004 |
| WO | WO-2004/096159 | 11/2004 |
| WO | WO-2007/047796 | 4/2007 |
| WO | WO-2009/002931 | 12/2008 |
| WO | WO-2011/084685 | 7/2011 |
| WO | WO-2013/096868 | 6/2013 |
| WO | WO-2014/151840 | 9/2014 |

OTHER PUBLICATIONS

[No Author Listed] Myc and Human cancer database. John Hopkins University School of medicine & john Hopkins health system. Last updated Apr. 14, 2013. Last accessed at http://www.myccancergene.org/site/cancerDB.asp?PageID=1 on Jul. 15, 2013.

Campana et al., Secretion of prosaposin, a multifunctional protein, by breast cancer cells. Biochim Biophys Acta. May 24, 1999; 1427(3): 392-400.

De Fraipont F et al: "Expression of the angiogenesis markers vascular endothelial growth factor-A, thrombospondin-1, and plateletderived endothelial cell growth factor in human sporadic adrenocortical tumors: Correlation with genotypic alterations", Journal of Clinical Endocrinology and Metabolism 2000 US LNKD—DOI:10.1210/JC.85.12.4734, vol. 85, No. 12, 2000, pp. 4734-4741.

Doll J A et al: "Thrombospondin-1, Vascular Endothelial Growth Factor and Fibroblast Growth FACTOR-2 are Key Functinal Regulators of Angiogenesis in the Prostate", Prostate, Wiley-Liss, New York, NY, US LNKD—DOI:10.1002/PROS.10025, vol. 49, Dec. 1, 2001 (Dec. 1, 2001), pp. 293-30.

Examination Report for AU 2016222333 dated Apr. 3, 2017.
Examination report for AU 2016222333 dated Jan. 23, 2018.
Examination Report on AU2010339794 dated Aug. 30, 2016.
Extended European Search Report for EP 16161100.9 dated Dec. 6, 2016.
Extended European Search Report for EP Application No. 15769874.7, dated Aug. 28, 2017, 9 pages.
GENBANK Submission; NIH/NCBI, Accession No. EAW54436. Venter et al., Dec. 18, 2006. 3 pages.
Gopalakrishnan et al., Purified recombinant human prosaposin forms oligomers that bind procathepsin D and affect its autoactivation. Biochem J. Nov. 1, 2004;383(Pt. 3):507-15.
Hu Siyi et al: "Prosaposin down-modulation decreases metastatic prostate cancer cell adhesion, migration, and invasion", Molecular Cancer, Biomed Central, London, GB, vol. 9, No. 1, Feb. 4, 2010 (Feb. 4, 2010), p. 30.
International Preliminary Report on Patentability for PCT/US2012/071424 (C1233.70048WA00) dated May 21, 2015.

(Continued)

*Primary Examiner* — Fred H Reynolds
(74) *Attorney, Agent, or Firm* — Foley & Lardner LLP

(57) ABSTRACT

Provided herein are cyclic prosaposin peptides and compositions and uses thereof. Exemplary uses include use in the treatment of cancer or in the treatment of inflammatory diseases or disorders.

4 Claims, 21 Drawing Sheets

Specification includes a Sequence Listing.

(56) References Cited

OTHER PUBLICATIONS

International Search Report and Written Opinion for International Application PCT/US2008/067899, dated Dec. 28, 2010, 25 pages.
International Search Report and Written Opinion for International Application PCT/US2010/061007, dated Aug. 30, 2011, 10 pages.
International Search Report and Written Opinion for International Application PCT/US2015/022745, dated Aug. 12, 2015, 9 pages.
Kalas et al., Oncogenes and angiogenesis: down-regulation of thromospondin-1 in normal fibroblasts exposed to factors from cancer cells harboring mutant ras. Cancer Res. Oct. 1, 2005;65(19):8878-86.
Kang Soo-Young et al: "Prosaposin inhibits tumor metastasis via paracrine and endocrine stimulation of stromal p53 and Tsp-1.", Proceedings of the National Academy of Sciences of the United States of America Jul. 21, 2009 LNKD—PUBMED: 19581582, vol. 106, No. 29, Jul. 21, 2009 (Jul. 21, 2009), pp. 12115-12120.
Koochekpour et al., Prosaposin is an AR-target gene and its neurotrophic domain upregulates AR expression and activity in prostate stromal cells. J Cell Biochem. Aug. 15, 2008;104(6):2272-85.
Koochekpour et al., Prosposin is a novel androgen-regulated gene in prostate cancer cell line LNCaP. J Cell Biochem. Jun. 1, 2007;101(3):631-41.
Koochekpour S et al: "Amplification and overexpression of prosaposin in prostate cancer", Genes Chromosomes and Cancer 200512 US LNKD—DOI:10.1002/GCC.20249, vol. 44, No. 4, Dec. 2005 (Dec. 2005), pp. 351-364.
Koochekpour, Psap (prosaposin (variant Gaucher disease and variant metachromatic leukodystrophy)). Atlas Genet Cytogenet Oncol Haematol. 2007;10:370-384.
Lee et al., Saposin C promotes survival and prevents apoptosis via P13K/Akt-dependent pathway in prostate cancer cells. Mol Cancer. Nov. 17, 2004; 3:31.
Morimoto et al., "Saposin A: second cerebrosidase activator protein," Proc. Natl. Acad. Sci., 86, pp. 3389-93, May 1989.
O'Brien et al., Coding of two sphingolipid activator proteins (SAP-1 and SAP-2) by same genetic locus. Science.Aug. 26, 1988;241 (4869):1098-101.
O'Brien et al., Saposin proteins: structure, function, and role in human lysosomal storage disorders. FASEB J. Mar. 1, 1991;5(3):301-8.
Office Action for CA 2,682,171 dated Feb. 11, 2016.
Office Action on EP 10842644.6 dated Sep. 29, 2016.
Office Action issued in co-pending U.S. Appl. No. 13/516,511 dated Mar. 26, 2018.
Panigone et al., Up-regulation of prosaposin by the retinoid HPR and the effect on ceramide production and integrin receptors. Faseb J. Jun. 2001; 15(8):1475-7.
Qi et al., Functional human saposins expressed in *Escherichia coli*. Evidence for binding and activation properties of saposins C with acid beta-glucosidase. J Biol Chem. Jun. 17, 1994; 269(24):1674-53.
Venter et al., prosaposin (variant Gaucher disease and variant metachroatic leukodystrophy), isoform CRA_a [*Homo sapiens*], Genbank Accession EAW54436.1, Dec. 18, 2006.
Vogelstein et al., p53: The most frequently altered gene in human cancers, nature education. 2012;3(9):6. Last accessed at http://www.nature.com/scitable/topicpage/p53-the-most-frequently-altered-gene-in-14192717 on Jul. 15, 2013.
Yabkowitz et al., Motility of human carcinoma cells in response to thrombospondin: relationship to metastatic potential and thrombospondin structural domains. Cancer Res. Jan. 15, 1993;53(2):378-87.
Notice of Allowance issued in co-pending U.S. Appl. No. 16/379,193, dated Jan. 22, 2020.
Lopez-Dee et al., "Thrombospondin-1 type 1 repeats in a model of inflammatory bowel disease: transcript profile and therapeutic effects," PLo5 ONE, vol. 7, Issue 4, 13 pages (Apr. 3, 2012).
Lopez-Dee et al., "Thrombospondin-1: Multiple Paths to Inflammation," *Mediators of Inflammation*, vol. 2011, 10 pages (May 2011).
The instructions from STN/CAS for Searching Polypeptide Sequences, pamphlet CAS2537-1108 (2008).
The Pharmaceutical Technology Editors, "Peptide Pegylation: The Next Generation," Pharm. Tech (2011) S3.
GenBank entry KHN41504, entered Dec. 17, 2014.

Cyclic DWLPK (SEQ ID NO: 1)

CYCLIC PROSAPOSIN PEPTIDES AND USES THEREOF

RELATED APPLICATIONS

This application is a Divisional of U.S. patent application Ser. No. 15/128,617, filed Sep. 23, 2016, which is the U.S. National Stage of International Patent Application No. PCT/US2015/022745, filed Mar. 26, 2015, which claims priority from U.S. Provisional Patent Application No. 61/970,853, filed Mar. 26, 2014. The contents of these applications are incorporated herein by reference in their entirety.

GOVERNMENT SUPPORT

This invention was made with government support under R01CA135417 awarded by the National Institutes of Health. The government has certain rights in the invention.

BACKGROUND OF INVENTION

Cancer remains a major public health concern. For example, an estimated 7.6 million deaths from cancer occurred in 2008. Many cancers are still untreatable or treatments are suboptimal, either being only partially effective or having undesirable side-effects like toxicity.

Inflammatory diseases and disorders are also a major public health concern and also have similar treatment issues as cancer.

SUMMARY OF INVENTION

Aspects of the disclosure are based in part on the discovery that cyclic prosaposin peptides, such as cyclic peptides having the sequence DWLPK (SEQ ID NO: 1), are both more stable and more effective than linear prosaposin peptides for treatment of an animal model of cancer. Surprisingly, the cyclic DWLPK (SEQ ID NO: 1) peptide was found to be more effective at stimulating thrombospondin-1 (Tsp-1) in vitro compared to a cyclic peptide having a substitution of glycine at position 3 (i.e., DWGPK, SEQ ID NO: 2). This data was unexpected because the opposite result was obtained with linear prosaposin peptides, in which linear DWGPK (SEQ ID NO: 2) was found to have better activity than linear DWLPK (SEQ ID NO: 1). Additionally, it was found that the cyclic DWLPK (SEQ ID NO: 1) peptide caused no toxicity to the liver or spleen of mice treated with the peptide.

Other aspects of the disclosure are based in part on the discovery that cyclic DWLPK (SEQ ID NO: 1) is effective for treating a mouse model of Crohn's disease.

Accordingly, aspects of the disclosure relate to cyclic prosaposin peptides, e.g., DWLPK (SEQ ID NO: 1), as well as compositions and methods utilizing such peptides.

Some aspects of the disclosure relate to a method for treating a subject having cancer, the method comprises administering to a subject having cancer an effective amount of a cyclic peptide to treat the cancer, wherein the amino acid sequence of the cyclic peptide is DWLPK (SEQ ID NO: 1). In some embodiments, the cancer is ovarian cancer or melanoma.

Other aspects relate to a composition for use in treating cancer, the composition comprising a cyclic peptide, wherein the amino acid sequence of the cyclic peptide is DWLPK (SEQ ID NO: 1). In some embodiments, the cancer is ovarian cancer or melanoma.

Yet other aspects of the disclosure relate to a method for treating a subject having an inflammatory disease or disorder, the method comprises administering to a subject having an inflammatory disease or disorder an effective amount of a cyclic peptide to treat the inflammatory disease or disorder, wherein the amino acid sequence of the cyclic peptide is DWLPK (SEQ ID NO: 1). In some embodiments, the inflammatory disease or disorder is rheumatoid arthritis, age-related macular degeneration (AMD). Crohn's disease, psoriasis, or atherosclerosis. In some embodiments, the inflammatory disease or disorder is Crohn's disease.

Other aspects of the disclosure relate to a composition for use in treating an inflammatory disease or disorder, the composition comprising a cyclic peptide, wherein the amino acid sequence of the cyclic peptide is DWLPK (SEQ ID NO: 1). In some embodiments, the inflammatory disease or disorder is rheumatoid arthritis, age-related macular degeneration (AMD), Crohn's disease, psoriasis, or atherosclerosis. In some embodiments, the inflammatory disease or disorder is Crohn's disease.

Other aspects of the disclosure relate to a method for stimulating thrombospondin-1 (Tsp-1) expression, the method comprising: administering to a subject in need thereof an effective amount of a cyclic peptide to stimulate Tsp-1 expression, wherein the amino acid sequence of the cyclic peptide is DWLPK (SEQ ID NO: 1).

Aspects of the disclosure relate to a cyclic Psap peptide. In some embodiments, the cyclic Psap peptide comprises the amino acid sequence DWLPK (SEQ ID NO: 1), dWLPK (SEQ ID NO: 3, lower case d indicates D-amino acid), DWGPK (SEQ ID NO: 2), or dWGPK (SEQ ID NO: 4, lower case d indicates D-amino acid). In some embodiments, the amino acid sequence of the cyclic Psap peptide is DWLPK (SEQ ID NO: 1), dWLPK (SEQ ID NO: 3, lower case d indicates D-amino acid), DWGPK (SEQ ID NO: 2), or dWGPK (SEQ ID NO: 4, lower case d indicates D-amino acid). In some embodiments, the cyclic Psap peptide comprises the amino acid sequence DWLPK (SEQ ID NO: 1). In some embodiments, the amino acid sequence of the cyclic Psap peptide is DWLPK (SEQ ID NO: 1).

Other aspects of the disclosure relate to compositions comprising a cyclic Psap peptide as described herein. In some embodiments, the composition is a pharmaceutical composition. In some embodiments, the composition comprises a cyclic Psap peptide as described herein and a pharmaceutically-acceptable carrier.

The details of one or more embodiments of the disclosure are set forth in the description below. Other features or advantages of the present disclosure will be apparent from the following drawings and detailed description of several embodiments, and also from the appending claims.

BRIEF DESCRIPTION OF DRAWINGS

The following drawings form part of the present specification and are included to further demonstrate certain aspects of the present disclosure, which can be better understood by reference to one or more of these drawings in combination with the detailed description of specific embodiments presented herein.

FIG. 12A is a western blot of Tsp-1 and β-actin in WI-38 lung fibroblasts that were untreated (−) or treated with native DWLP (SEQ ID NO: 6), L-amino acid, prosaposin peptide (WT), dWlP (SEQ ID NO: 5, lower case d and l indicate D-amino acids) prosaposin peptide (d1,3) or DwLp (SEQ ID NO: 7, lower case w and p indicate D-amino acids) prosaposin peptide (d2,4); FIG. 12B is a western blot of Tsp-1 and β-actin in mouse lung tissue harvested from mice treated with metastatic prostate cancer cell conditioned media alone (−) or in combination with DWLP (SEQ ID NO: 6) prosaposin peptide (WT) or dWlP (SEQ ID NO: 5, lower case d and l indicate D-amino acids) prosaposin peptide (d1,3 peptide) at doses of 10 and 30 mg/kg/day for 3 days; FIG. 12C is a western blot of CD36 and β-actin in 8 patient derived ovarian cancer cell lines; FIG. 12D is a plot of cell number as measured by Wst-1 assay of a patient derived ovarian cancer cell line treated with 1 µM recombinant human Tsp-1 (rhTsp-1) for 24, 48 and 72 hours; and FIG. 12E is a FACS analysis of Annexin V and PI of a patient derived ovarian cancer cell line treated with 1 µM recombinant human Tsp-1 (rhTsp-1) for 48 hours.

FIG. 13A is a plot of relative luciferase intensity of metastatic PDX ovarian tumors that were treated with saline (control), cisplatin 4 mg/kg/QOD (Cisplatin) and dWlP (SEQ ID NO: 5) prosaposin peptide (40 mg/kg QD); FIG. 13B shows luciferase imaging of two control treated mice and two dWlP (SEQ ID NO: 5) prosaposin peptide treated mice at day 17 (treatment day 0) and day 48 (treatment day 31), with each image having a luminescence scale to the right of the image that is shown in ×10$^8$ units of radiance (p/sec/cm$^2$/sr), with the minimum on the scale being 0.05e6 and the maximum on the scale being 1.00e8; FIG. 13C shows photographs of the livers of mice bearing metastatic PDX ovarian tumors treated with saline (control) or dWlP (SEQ ID NO: 5) prosaposin peptide (Peptide); FIG. 13D shows H&E staining of the liver of a mouse bearing metastatic PDX ovarian tumors treated with saline (control) or dWlP (SEQ ID NO: 5) prosaposin peptide (Peptide). Right panels are 5× magnification and left panels are 20× magnification; and FIG. 13E is a FACS analysis of GR1$^+$/Cd11b$^+$ cells in the peritoneal fluid of mice control and dWlP (SEQ ID NO: 5) prosaposin peptide (Peptide) treated mice bearing metastatic PDX ovarian tumors after 48 days.

FIG. 14A is a western blot of Tsp-1 and β-actin in WI-38 lung fibroblasts that were untreated (−), treated with dWlP (SEQ ID NO: 5) prosaposin peptide (d1,3, "L"), or with cyclic DWLPK (SEQ ID NO: 1) prosaposin peptide ("C"); FIG. 14B shows an ELISA of Tsp-1 expression in WI-38 lung fibroblasts that were untreated (−), treated with dWlP (SEQ ID NO: 5) prosaposin peptide (d1,3), or with cyclic DWLPK (SEQ ID NO: 1) prosaposin peptide after up to 24 hours of incubation in human plasma at 37° C.; FIG. 14C is a plot of relative luciferase intensity of metastatic PDX ovarian tumors that were treated with saline (control) or cyclic DWLPK (SEQ ID NO: 1) prosaposin peptide (10 mg/kg QD); FIG. 14D is a plot of average metastatic lesion in saline (control) treated mice and cyclic DWLPK (SEQ ID NO: 1) prosaposin peptide (Peptide) treated mice; FIG. 14E is an immunofluorescent staining of Gr1 and Tsp-1 expression in metastatic lesions of control treated mice and cyclic DWLPK (SEQ ID NO: 1) prosaposin peptide (Peptide) treated mice; and FIG. 14F shows the immunohistochemistry (leftmost panels) of Tsp-1 expression and immunofluorescent staining of TUNEL and DAPI of metastatic lesions in control and cyclic DWLPK (SEQ ID NO: 1) prosaposin peptide (Peptide) treated mice.

FIGS. 15A-15C show the expression of CD36 in normal human ovaries (Magnification: A=5×, B=10×, C=20×); FIG. 15N is a plot of prosaposin (Psap) staining indices of normal human ovaries, primary human ovarian tumors, human ovarian cancer metastases, and human ovarian cancer lymph node metastases.

DETAILED DESCRIPTION OF INVENTION

Figure 1:
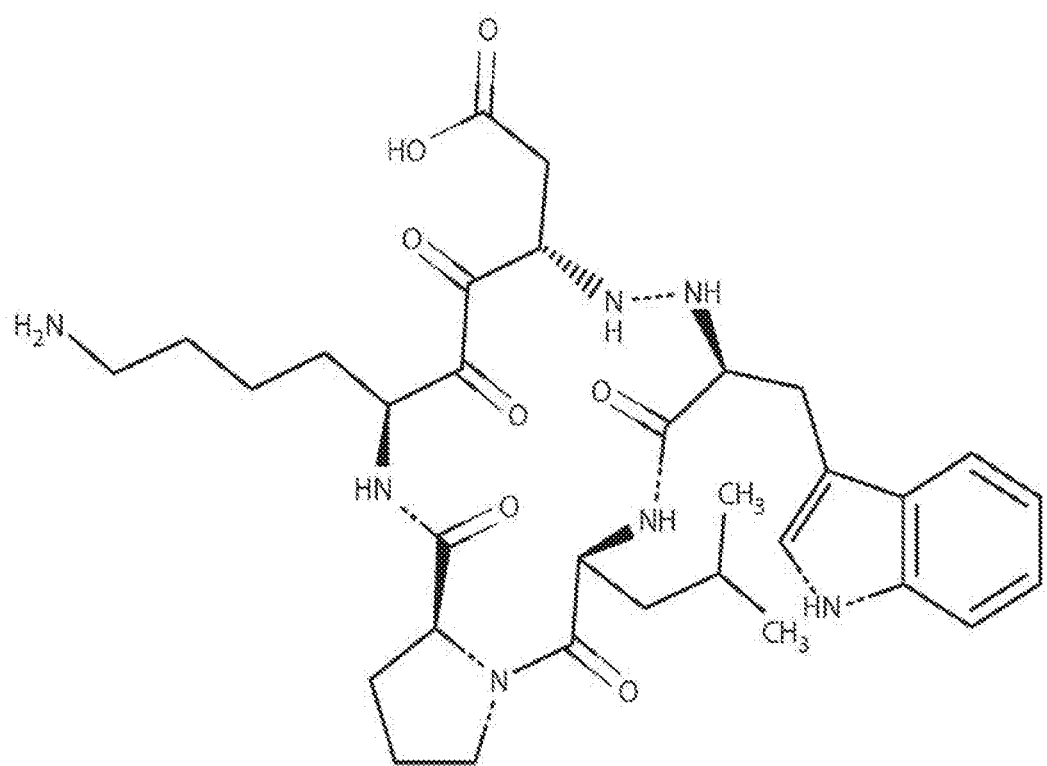
FIG. 1 is an exemplary schematic of cyclic DWLPK (SEQ ID NO: 1).

Prosaposin peptides (referred to herein as Psap peptides), which were originally derived from fragments of Saposin A, were previously shown to be effective for treating multiple types of cancers when used in linear form (see, e.g., PCT publications WO2009002931 WO/2011/084,685 and WO/2013/096,868, and U.S. patent application Ser. Nos. 12/640,788 and 13/516,511, all of which are incorporated herein by reference in their entirety).

As described herein, it has been discovered that cyclic Psap peptides, in particular cyclic DWLPK (SEQ ID NO: 1), are unexpectedly both more stable and more effective than linear Psap peptides. In addition, cyclic DWLPK (SEQ ID NO: 1) was found to have no toxic effect on the liver or spleen. Further, it was found that cyclic DWLPK (SEQ ID NO: 1) had better activity than other cyclic versions of amino-acid-substituted peptides (e.g., DWGPK, SEQ ID NO: 2). This finding was surprising because linear version of the substituted peptides were found to be more active than a linear version of DWLPK (SEQ ID NO: 1).

Also as described herein, it has been discovered that the cyclic Psap peptide DWLPK (SEQ ID NO: 1) was effective in a mouse model of Crohn's disease. Without wishing to be bound by theory, it is believed that the cyclic Psap peptide activates or enhances Tsp-1 expression and that the Tsp-1 expression reduces inflammation associated with Crohn's disease. Tsp-1 has been shown previously to be secreted in response to inflammation, promoting the resolution of the inflammatory process and facilitating phagocytosis of damaged cells (see, e.g., Lopez-Dee et al. Thrombospondin-1: Multiple Paths to Inflammation, (2011) Mediators of Inflammation; Vol. 2011; Article ID 296069). Thus, as a therapeutic effect of the cyclic Psap peptide was seen in a model of Crohn's disease, which is an exemplary inflammatory disease, it is believed that the cyclic Psap peptide will also be effective for treating other inflammatory diseases, such as rheumatoid arthritis and psoriasis, as well as other diseases in which inflammation is involved, e.g., inflammatory disorders such as atherosclerosis, and age-related macular degeneration (AMD).

Accordingly, aspects of the disclosure relate to cyclic Psap peptides, as well as their use in compositions and methods for treating diseases, such as cancer and inflammatory disorders or diseases as well as other diseases in which inflammation is involved.

Cyclic Psap Peptides

Prosaposin (Psap) is the Saposin precursor protein made up of approximately 524-527 amino acids which includes a 16 amino acids signal peptide. The full-length precursor polypeptide undergoes co-translational glycosylation and modification in the endoplasmic reticulum and Golgi system to yield a 70-72 kDa precursor protein. After transport to the lysosome, cathepsin D participates in its proteolytic processing to yield intermediate molecular forms of 35 to 53 kDa and then to a 13-kDa glycoprotein and finally to the mature 8-11 kDa partially glycosylated forms of individual Saposin molecules (O'Brien J. S., and Kishimoto Y, The FASEB J., 5: 301-8, 1991; Kishimoto Y. et al., J. Lipid Res. 33:1255-67, 1992). Prosaposin is processed into 4 cleavage products: Saposins A, B, C, and D. The amino acid sequences of Psap preproprotein isoforms A, B, and C and the amino acid sequence of cleavage product Saposin A are below:

```
Psap Preproprotein Isoform A
                                          (SEQ ID NO: 9)
MYALFLLASLLGAALAGPVLGLKECTRGSAVWCQNVKTASDCGAVKHC

LQTVWNKPTVKSLPCDICKDVVTAAGDMLKDNATEEEILVYLEKTCDW
```

```
LPKPNMSASCKEIVDSYLPVILDIIKGEMSRPGEVCSALNLCESLQKH

LAELNHQKQLESNKIPELDMTEVVAPFMANIPLLLYPQDGPRSKPQPK

DNGDVCQDCIQMVTDIQTAVRTNSTFVQALVEHVKEECDRLGPGMADI

CKNYISQYSEIAIQMMMHMQPKEICALVGFCDEVKEMPMQTLVPAKVA

SKNVIPALELVEPIKKHEVPAKSDVYCEVCEFLVKEVTKLIDNNKTEK

EILDAFDKMCSKLPKSLSEECQEVVDTYGSSILSILLEEVSPELVCSM

LHLCSGTRLPALTVHVTQPKDGGFCEVCKKLVGYLDRNLEKNSTKQEI

LAALEKGCSFLPDPYQKQCDQFVAEYEPVLIEILVEVMDPSFVCLKIG

ACPSAHKPLLGTEKCIWGPSYWCQNTETAAQCNAVEHCKRHVWN
```

```
Psap Preproprotein Isoform B
                                         (SEQ ID NO: 10)
MYALFLLASLLGAALAGPVLGLKECTRGSAVWCQNVKTASDCGAVKHC

LQTVWNKPTVKSLPCDICKDVVTAAGDMLKDNATEEEILVYLEKTCDW

LPKPNMSASCKEIVDSYLPVILDIIKGEMSRPGEVCSALNLCESLQKH

LAELNHQKQLESNKIPELDMTEVVAPFMANIPLLLYPQDGPRSKPQPK

DNGDVCQDCIQMVTDIQTAVRTNSTFVQALVEHVKEECDRLGPGMADI

CKNYISQYSEIAIQMMMHMQDQQPKEICALVGFCDEVKEMPMQTLVPA

KVASKNVIPALELVEPIKKHEVPAKSDVYCEVCEFLVKEVTKLIDNNK

TEKEILDAFDKMCSKLPKSLSEECQEVVDTYGSSILSILLEEVSPELV

CSMLHLCSGTRLPALTVHVTQPKDGGFCEVCKKLVGYLDRNLEKNSTK

QEILAALEKGCSFLPDPYQKQCDQFVAEYEPVLIEILVEVMDPSFVCL

KIGACPSAHKPLLGTEKCIWGPSYWCQNTETAAQCNAVEHCKRHVWN
```

```
Psap Preproprotein Isoform C
                                         (SEQ ID NO: 11)
MYALFLLASLLGAALAGPVLGLKECTRGSAVWCQNVKTASDCGAVKHC

LQTVWNKPTVKSLPCDICKDVVTAAGDMLKDNATEEEILVYLEKTCDW

LPKPNMSASCKEIVDSYLPVILDIIKGEMSRPGEVCSALNLCESLQKH

LAELNHQKQLESNKIPELDMTEVVAPFMANIPLLLYPQDGPRSKPQPK

DNGDVCQDCIQMVTDIQTAVRTNSTFVQALVEHVKEECDRLGPGMADI

CKNYISQYSEIAIQMMMHMDQQPKEICALVGFCDEVKEMPMQTLVPAK

VASKNVIPALELVEPIKKHEVPAKSDVYCEVCEFLVKEVTKLIDNNKT

EKEILDAFDKMCSKLPKSLSEECQEVVDTYGSSILSILLEEVSPELVC

SMLHLCSGTRLPALTVHVTQPKDGGFCEVCKKLVGYLDRNLEKNSTKQ

EILAALEKGCSFLPDPYQKQCDQFVAEYEPVLIEILVEVMDPSFVCLK

IGACPSAHKPLLGTEKCIWGPSYWCQNTETAAQCNAVEHCKRHVWN
```

```
Saposin A
                                         (SEQ ID NO: 12)
SLPCDICKDVVTAAGDMLKDNATEEEILVYLEKTCDWLPKPNMSASCK

EIVDSYLPVILDIIKGEMSRPGEVCSALNLCES
```

Aspects of the disclosure relate to a cyclic Psap peptide, compositions comprising a cyclic Psap peptide, and uses thereof. In some embodiments, the cyclic Psap peptide comprises the amino acid sequence DWLPK (SEQ ID NO: 1), dWLPK (SEQ ID NO: 3, lower case d indicates D-amino acid), DWGPK (SEQ ID NO: 2), or dWGPK (SEQ ID NO: 4, lower case d indicates D-amino acid). In some embodiments, the amino acid sequence of the cyclic Psap peptide is DWLPK (SEQ ID NO: 1), dWLPK (SEQ ID NO: 3, lower case d indicates D-amino acid), DWGPK (SEQ ID NO: 2), or dWGPK (SEQ ID NO: 4, lower case d indicates D-amino acid). In some embodiments, the cyclic Psap peptide comprises the amino acid sequence DWLPK (SEQ ID NO: 1). In some embodiments, the amino acid sequence of the cyclic Psap peptide is DWLPK (SEQ ID NO: 1).

In some embodiments, the cyclic peptide is less than 10, less than 9, less than 8, less than 7, less than 6, or 5 amino acids in length. In some embodiments, the cyclic peptide is between 5-10, 5-9, 5-8, 5-7 or 5-6 amino acids in length. In some embodiments, the cyclic peptide is 5 amino acids in length.

Peptides described herein can be chemically synthesized and isolated by biochemical methods that are well known in the art such as solid phase peptide synthesis using t-Boc (tert-butyloxycarbonyl) or FMOC (9-fluorenylmethloxycarbonyl) protection group described in "Peptide synthesis and applications" in Methods in molecular biology Vol. 298, Ed. by John Howl and "Chemistry of Peptide Synthesis" by N. Leo Benoiton, 2005, CRC Press, (ISBN-13: 978-1574444544) and "Chemical Approaches to the Synthesis of Peptides and Proteins" by P. Lloyd-Williams, et al., 1997, CRC-Press, (ISBN-13: 978-0849391422). Solid phase peptide synthesis, developed by R. B. Merrifield, 1963, J. Am. Chem. Soc. 85 (14): 2149-2154, was a major breakthrough allowing for the chemical synthesis of peptides and small proteins.

Cyclic Psap peptides can be synthesized using any method known in the art. Exemplary methods of synthesis include, but are not limited to, recombinant synthesis, liquid-phase synthesis, Solid-phase synthesis, or chemical ligation (see, e.g., Molecular Cloning: A Laboratory Manual, J. Sambrook, et al., eds., Third Edition, Cold Spring Harbor Laboratory Press, Cold Spring Harbor, N.Y., 2001; Current Protocols in Molecular Biology, F. M. Ausubel, et al., eds., John Wiley & Sons, Inc., New York; Schnolzer, M. A., P.; Jones, A.; Alewood, D.; Kent, S. B. H. (2007). "In Situ Neutralization in Boc-chemistry Solid Phase Peptide Synthesis", Int. J. Peptide Res. Therap. 13 (1-2): 31-44; Albericio, F. (2000), Solid-Phase Synthesis: A Practical Guide (1 ed.), Boca Raton: CRC Press, p. 848; and Nilsson B L, Soellner M B, Raines R T (2005), "Chemical Synthesis of Proteins", Annu. Rev. Biophys. Biomol. Struct. 34: 91-118; and U.S. Pat. Nos. 4,749,742, 4,794,150, 5,552,471, 5,637,719, 6,001,966, 7,038,103, 7,094,943, 7,176,282, and 7,645,858, the entirety of which are incorporated herein by reference). Psap peptides and methods of making Psap peptides are also known in the art (see, e.g., PCT publications WO2009002931, WO/2011/084,685 and WO/2013/096,868, all of which are incorporated herein by reference in their entirety). Cyclic peptides are polypeptide chains that are linked together with a peptide bond or other covalent bond, forming a circular structure. Methods of design and synthesis of cyclic peptides are well known in the art (see, e.g. as described in U.S. Pat. Nos. 5,596,078; 5,990,273; 7,589,170 and U.S. Patent Application No. 20080287649) and commercially available (see, e.g., cyclic peptide synthesis services offered by Selleck Chemicals, Abbiotec, Abgent, AnaSpec Global Peptide Services, LLC., INVITROGEN™ and rPeptide, LLC or GenScript). Cyclic peptides may be circularized, e.g., head-to-tail (C-terminus to N-terminus), head-to-side chain, side-chain-to-tail, or side-chain-to-side-chain (see, e.g., White et al. Contemporary strategies for peptide macrocyclization, Nature Chemistry (2011); 3:509-524). A cyclization reagent, such as PyBOP (benzotriazol-1-yl-oxytripyrrolidinophosphonium hexafluorophosphate). BOP (benzotriazol-1-yl-oxy-tris-(dimethylamino)phosphonium hexa-fluorophosphate), DIPEA (N,N-diisopropylethylamine), DMTMM BF4 (4-(4,6-dimethoxy-1,3,5-triazin-2-yl)-4-methylmorpholinium tetrafluoroborate) or FDPP (pentafluorophenyl diphenylphosphinate) or combinations thereof, may be used during peptide synthesis or after peptide synthesis to induce circulization. An exemplary method involves use of a photolabile auxiliary, e.g., HnB (2-hydroxy-6-nitrobenzyl), in a ring-contraction strategy to cyclize a pentapeptide. After the introduction of this auxiliary onto the N-terminus of the peptide, the peptide is contacted with BOP and DIPEA, resulting an intramolecular O-to-N acyl transfer, which in turn results in the cyclic pentapeptide. The photolabile auxiliary can then be removed.

In some embodiments, the Psap peptide may be modified, for example, through oligomerization or polymerization (e.g., dimers, trimer, multimers, etc.), modifications of amino acid residues or peptide backbone, cross-linking, conjugation, pegylation, glycosylation, acetylation, phosphorylation, fusion to additional heterologous amino acid sequences (for example, an antibody or antibody Fc domain, serum transferrin or portions thereof, albumin, or transthyretin), or other modifications that substantially alter the stability, solubility, or other properties of the peptide while substantially retaining or enhancing therapeutic activity. Conjugation may be, e.g., to a polymer. Suitable polymers include, for example, polyethylene glycol (PEG), polyvinyl pyrrolidone, polyvinyl alcohol, polyamino acids, divinylether maleic anhydride, N-(2-Hydroxypropyl)-methacrylamide, dextran, dextran derivatives including dextran sulfate, polypropylene glycol, polyoxyethylated polyol, heparin, heparin fragments, polysaccharides, cellulose and cellulose derivatives, including methylcellulose and carboxymethyl cellulose, starch and starch derivatives, polyalkylene glycol and derivatives thereof, copolymers of polyalkylene glycols and derivatives thereof, polyvinyl ethyl ethers, and α,β-Poly[(2-hydroxyethyl)-DL-aspartamide, and the like, or mixtures thereof. Conjugation may be through a linker, e.g., a peptide or chemical linker. Methods of modifying peptides are well known in the art (see, e.g., U.S. Pat. Nos. 5,180,816, 5,596,078, 5,990,273, 5,766,897, 5,856,456, 6,423,685, 6,884,780, 7,610,156, 7,256,258, 7,589,170 and 7,022,673, and PCT publication WO 2010/014,616, the contents of which are incorporated herein by reference).

In some embodiments, the cyclic Psap peptide is functionally modified to enhance stability. In some embodiments, chemical modifications to the Psap peptide include, but are not limited to the inclusion of, alkyl, alkoxy, hydroxyalkyl, alkoxyalkyl, alkoxycarbonyl, alkenyl, alkynyl, cycloalkyl, amino, alkylamino, aminoalkyl, dialkylamino, aminodialkyl, halogen, heteroatom, carbocycle, carbocyclyl, carbocyclo, carbocyclic, aryl, aralkyl, aralkoxy, aryloxyalkyl, heterocycle, heterocyclyl, heterocyclic, heteroaryl, and/or aliphatic groups.

In some embodiments, the cyclic peptide is fused/conjugated to at least one therapeutic molecule.

In some embodiments, amino acid substitution variants of a cyclic Psap peptide resulting from substitution of one or more D-amino acids for the like L-amino acid are contemplated herein. In some embodiments, one D-amino acid substitution is present. In some embodiments, 2 or more D-amino acid substitutions are present. In some embodiments, 3, 4, or 5 D-amino acid substitutions are present. In some embodiments, the D-amino acid substitutions are evenly spaced, e.g., every other amino acid. In some embodiments, the D-amino acid substitution is for Aspartic Acid (D). The L and D convention for amino acid configuration refers not to the optical activity of the amino acid itself, but rather to the optical activity of the isomer of glyceraldehyde from which that amino acid can, in theory, be synthesized (D-glyceraldehyde is dextrorotary; L-glyceraldehyde is levorotary). Exemplary D amino acid substitution variants include cyclic dWLPK (SEQ ID NO: 3 lower case d indicates D-amino acid) and cyclic dWGPK (SEQ ID NO: 4, lower case d indicates D-amino acid).

The cyclic peptide described herein can further be modified or derivatized. The modified or derivatized polypeptides will typically substantially retain the activity of the base polypeptide (pre-modified/derivatized). Examples of modifications and derivatives are pegylation, glycosylation, acetylation, amidation, and phosphorylation. Methods of acetylation (e.g., N-terminal acetylation) and amidation (e.g., C-terminal amidation) are well known to those of skill in the art. Modifications, derivatives and methods of derivatizing polypeptides are described in Published International Application WO 2010/014,616, the contents of which are incorporated herein by reference.

In some embodiments, the cyclic peptide described herein can be conjugated or otherwise covalently attached to other molecules (e.g., using a chemical linker). One such form of attachment is through a non-amide linkage (e.g., a disulfide bond). In some embodiments, the cyclic peptide is linked to a polymer that enhances the serum half-life. In some embodiments, the cyclic peptide is covalently attached (e.g., via a linker molecule) to an antibody or a domain thereof suitable for enhancing the half-life of the molecule (e.g., one or more constant domains in an Fc domain). In some embodiments, the polypeptide is linked to an Fc domain (e.g., IgG, IgA, IgM, IgD, or IgE).

In some embodiments, the cyclic peptide described herein is linked to a non-amino acid polymer. Polymers such as polyethylene glycol can be used for the purpose of enhancing the serum half-life. Suitable polymers include, for example, polyethylene glycol (PEG), polyvinyl pyrrolidone, polyvinyl alcohol, polyamino acids, divinylether maleic anhydride, N-(2-Hydroxypropyl)-methacrylamide, dextran, dextran derivatives including dextran sulfate, polypropylene glycol, polyoxyethylated polyol, heparin, hepatin fragments, polysaccharides, cellulose and cellulose derivatives, including methylcellulose and carboxymethyl cellulose, starch and starch derivatives, polyalkylene glycol and derivatives thereof, copolymers of polyalkylene glycols and derivatives thereof, polyvinyl ethyl ethers, and α,β-Poly[(2-hydroxyethyl)-DL-aspartamide, and the like, or mixtures thereof. Such a polymer may or may not have its own biological activity. The polymers can be covalently or non-covalently conjugated to the cyclic peptide. Methods of conjugation for increasing serum half-life are known in the art, for example, in U.S. Pat. Nos. 5,180,816, 6,423,685, 6,884,780, and 7,022,673, which are hereby incorporated by reference in their entirety.

In some embodiments, the cyclic peptide is conjugated to a therapeutic molecule. In some embodiments, the therapeutic molecule is an anti-angiogenic therapeutic molecule, an anti-VEGF agent, a chemotherapeutic agent, or an anti-inflammatory agent.

The various versions of cyclic peptides described herein, e.g., modified, conjugated, or derivatized cyclic peptides, encompassed by the present disclosure are expected to retain a significant amount of the biological activity exhibited by the cyclic peptide (e.g., as reported in the Examples section herein). In some embodiments, about 100% of the activity is retained in a given assay. In some embodiments, about 90%, 80%, 70%, 60% or 50% of the activity is retained. One such activity is the ability to stimulate expression of Tsp-1. Stimulation of expression is a significant, reproducible amount of increased expression that occurs from contact of the cyclic peptide described herein with an appropriate target cell, as compared to an identical or sufficiently similar target cell (control target cell) that has not been contacted with the cyclic peptide. The methods for determining Tsp-1 expression induction activity are described herein and are also well known to one skilled in the art.

The amino acid abbreviations are shown below.
Alanine, Ala, A
Isoleucine, Ile, I
Leucine, Leu, L
Valine, Val, V
Phenylalanine, Phe, F
Tryptophan, Trp, W
Tyrosine, Tyr, Y
Asparagine, Asn, N
Cysteine, Cys, C
Glutamine, Gln, Q
Methionine, Met, M
Serine, Ser, S
Threonine, Thr, T
Aspartic acid, Asp, D
Glutamic acid, Glu, E
Arginine, Arg, R
Histidine, His, H
Lysine, Lys, K
Glycine, Gly, G
Proline, Pro, P Other Cyclic Peptide Modifications It is to be understood that modified versions of the cyclic peptides described herein are encompassed in the present disclosure. Modification to a cyclic peptide described herein can be performed as described in U.S. published application 20080090760 and/or U.S. published application 20060286636, each of which is incorporated herein by reference in its entirety. The following provides a non-limiting discussion of various other peptide modifications encompassed within the scope of the disclosure.

Encompassed by the present disclosure are chemical derivatives of a cyclic peptide described herein, so long as it substantially retains the activities of the non-derivatized cyclic peptide. A "chemical derivative" is a subset of peptide derivatives as described herein and refers to a subject cyclic peptide having one or more residues chemically derivatized by reaction of a functional side group. In addition to side group derivatizations, a chemical derivative can have one or more backbone modifications including alpha-amino substitutions such as N-methyl, N-ethyl, N-propyl and the like, and alpha-carbonyl substitutions such as thioester, thioamide, guanidino and the like. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides which contain one or more naturally occurring amino acid derivatives of the twenty standard amino acids. Also included as chemical derivatives are those peptides which contain one or more non-limiting, non-natural amino acids, examples include those available for peptide synthesis from commercial suppliers (e.g. Bachem Catalog, 2004 pp. 1-276). For examples: 4-hydroxyproline may be substituted for proline; 5-hydroxylysine may be substituted for lysine; 3-methylhistidine may be substituted for histidine; homoserine may be substituted for serine; ornithine may be substituted for lysine; β-alanine may be substituted for alanine; norleucine may be substituted for leucine; phenylglycine may be substituted for phenylalanine, and L-1,2,3,4-tetrahydronorharmane-3-carboxylic acid or H-β-(3-Benzothienyl)-Ala-OH may be substituted for tryptophan.

In certain embodiments, chemical modifications to the peptide include, but are not limited to the inclusion of, alkyl, alkoxy, hydroxyalkyl, alkoxyalkyl, alkoxycarbonyl, alkenyl, alkynyl, cycloalkyl, amino, alkylamino, aminoalkyl, dialkylamino, aminodialkyl, halogen, heteroatom, carbocycle, carbocyclyl, carbocyclo, carbocyclic, aryl, aralkyl, aralkoxy, aryloxyalkyl, heterocycle, heterocyclyl, heterocyclic, heteroaryl, and/or aliphatic groups.

The terms "alkyl", "alkoxy", "hydroxyalkyl", "alkoxyalkyl", and "alkoxycarbonyl", used alone or as part of a larger moiety includes both straight and branched chains containing one to twelve carbon atoms. The teams "alkenyl" and "alkynyl" used alone or as part of a larger moiety shall include both straight and branched chains containing two to twelve carbon atoms. The term "cycloalkyl" used alone or as part of a larger moiety shall include cyclic C3-C12 hydrocarbons which are completely saturated or which contain one or more units of unsaturation, but which are not aromatic. Lower alkyl refers to an alkyl group containing 1-6 carbons.

The team "amino" refers to an NH2 group. The term "alkylamino" or "aminoalkyl" refers to an amino group wherein one of the hydrogen atoms is replaced by an alkyl group. The term "dialkylamino" or "aminodialkyl" refers to an amino group wherein the hydrogen atoms are replaced by alkyl groups, wherein the alkyl group may be the same or different. The term "halogen" means F, Cl, Br, or I. The term "heteroatom" means nitrogen, oxygen, or sulfur with a carbon ring structure and includes any oxidized form of nitrogen and sulfur, and the quaternized form of any basic nitrogen. Also the term "nitrogen" includes a substitutable nitrogen of a heterocyclic ring. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl) or NR+ (as in N-substituted pyrrolidinyl). The terms "carbocycle", "carbocyclyl", "carbocyclo", or "carbocyclic" as used herein means an aliphatic ring system having three to fourteen members. The terms "carbocycle", "carbocyclyl", "carbocyclo", or "carbocyclic" whether saturated or partially unsaturated, also refers to rings that are optionally substituted. The terms "carbocycle", "carbocyclyl", "carbocyclo", or "carbocyclic" also include aliphatic rings that are fused to one or more aromatic or nonaromatic rings, such as in a decahydronaphthyl or tetrahydronaphthyl, where the radical or point of attachment is on the aliphatic ring.

The term "aryl" used alone or as part of a larger moiety as in "aralkyl", "aralkoxy", or "aryloxyalkyl", refers to aromatic ring groups having six to fourteen members, such as phenyl, benzyl, phenethyl, 1-naphthyl, 2-naphthyl, 1-anthracyl and 2-anthracyl. The term "aryl" also refers to rings that are optionally substituted. The term "aryl" may be used interchangeably with the term "aryl ring". "Aryl" also includes fused polycyclic aromatic ring systems in which an aromatic ring is fused to one or more rings. Examples include 1-naphthyl, 2-naphthyl, 1-anthracyl and 2-anthracyl.

Also included within the scope of the term "aryl", as it is used herein, is a group in which an aromatic ring is fused to one or more non-aromatic rings, such as in an indanyl, phenanthridinyl, or tetrahydronaphthyl, where the radical or point of attachment is on the aromatic ring.

The term "heterocycle", "heterocyclyl", or "heterocyclic" as used herein includes non-aromatic ring systems having four to fourteen members, preferably five to ten, in which one or more ring carbons, preferably one to four, are each replaced by a heteroatom. Examples of heterocyclic rings include 3-1H-benzimidazol-2-one, (1-substituted)-2-oxobenzimidazol-3-yl, 2-tetrahydro-furanyl, 3-tetrahydrofuranyl, 2-tetrahydropyranyl, 3-tetrahydropyranyl, 4-tetrahydropyranyl, [1,3]-dioxolanyl, [1,3]-dithiolanyl, [1,3]-dioxanyl, 2-tetra-hydro-thiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidinyl, benzoxanyl, benzopyrrolidinyl, benzopiperidinyl, benzoxolanyl, benzothiolanyl, and benzothienyl. Also included within the scope of the term "heterocyclyl" or "heterocyclic", as it is used herein, is a group in which a non-aromatic heteroatom-containing ring is fused to one or more aromatic or non-aromatic rings, such as in an indolinyl, chromanyl, phenanthridinyl, or tetrahydroquinolinyl, where the radical or point of attachment is on the non-aromatic heteroatom-containing ring. The term "heterocycle", "heterocyclyl", or "heterocyclic" whether saturated or partially unsaturated, also refers to rings that are optionally substituted.

The term "heteroaryl", used alone or as part of a larger moiety as in "heteroaralkyl" or "heteroarylalkoxy", refers to heteroaromatic ring groups having five to fourteen members. Examples of heteroaryl rings include 2-furanyl, 3-furanyl, 3-furazanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 1-pyrazolyl, 2-pyrazolyl, 3-pyrazolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indazolyl, isoindolyl, acridinyl, and benzoisoxazolyl. Also included within the scope of the term "heteroaryl", as it is used herein, is a group in which a heteroatomic ring is fused to one or more aromatic or nonaromatic rings where the radical or point of attachment is on the heteroaromatic ring. Examples include tetrahydroquinolinyl, tetrahydroisoquinolinyl, and pyrido[3,4-d]pyrimidinyl. The term "heteroaryl" also refers to rings that are optionally substituted. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Examples of suitable substituents on any unsaturated carbon atom of an aryl, heteroaryl, aralkyl, or heteroaralkyl group include a halogen, —R0, —OR0, —SR0, 1,2-methylene-dioxy, 1,2-ethylenedioxy, protected OH (such as acyloxy), phenyl (Ph), substituted Ph, —O(Ph), substituted —O(Ph), —CH2(Ph), substituted —CH2(Ph), CH2CH2(Ph), substituted —CH2CH2(Ph), —NO2, —CN, —N(R0)2, —NR0C(O)R0, NR0C(O)N(R0)2, NR0CO2R0, —NR0NR0C(O)R0, —NR0NR0C(O)N(R0)2, —NR0NR0C2R0, C(O)C(O)R0, C(O)CH2C(O)R0, —CO2R0, —C(O)R0, —C(O)N(R0)2, —OC(O)N(R0)2, S(O)2R0, —SO2N(R0)2, —S(O)R0, —NR0SO2N(R0)2, —NR0SO2R0, —C(=S)N(R0)2, C(=NH)N(R0)2, (CH2)yNHC(O)R0, and —(CH2)yNHC(O)CH(V—R0)(R0); wherein each R0 is independently selected from hydrogen, a substituted or unsubstituted aliphatic group, an unsubstituted heteroaryl or heterocyclic ring, phenyl (Ph), substituted Ph, O(Ph), substituted —O(Ph), —CH2 (Ph), or substituted —CH2(Ph); y is 0-6; and V is a linker group. Examples of substituents on the aliphatic group or the phenyl ring of R0 include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, and haloalkyl.

An aliphatic group or a non-aromatic heterocyclic ring or a fused aryl or heteroaryl ring may contain one or more substituents. Examples of suitable substituents on any saturated carbon of an aliphatic group or of a non-aromatic heterocyclic ring or a fused aryl or heteroaryl ring include those listed above for the unsaturated carbon of an aryl or heteroaryl group and the following: =O, =S, =NNHR*, =NN(R*)2, =N—, =NNHC(O)R*, =NNHCO2(alkyl), =NNHSO2 (alkyl), or =NR*, where each R* is independently selected from hydrogen, an unsubstituted aliphatic group, or a substituted aliphatic group. Examples of substituents on the aliphatic group include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, and haloalkyl.

Suitable substituents on the nitrogen of a non-aromatic heterocyclic ring include R+, —N(R+)2, —C(O)R+, —CO2R+, —C(O)C(O)R+, —C(O)CH2C(O)R+, —SO2R+, —SO2N(R+)2, C(=S)N(R+)2, —C(=NH)—N(R+)2, and —NR+SO2R+; wherein each R+ is independently selected from hydrogen, an aliphatic group, a substituted aliphatic group, phenyl (Ph), substituted Ph, —O(Ph), substituted —O(Ph), —CH2(Ph), substituted —CH2(Ph), or an unsubstituted heteroaryl or heterocyclic ring. Examples of substituents on the aliphatic group or the phenyl ring include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, and haloalkyl.

In certain embodiments, the peptide monomers described herein are dimerized or multimerized by covalent attachment to at least one linker moiety. The linker moiety is preferably, although not necessarily, a C1-12 linking moiety optionally terminated with one or two —NH— linkages and optionally substituted at one or more available carbon atoms with a lower alkyl substituent. Preferably the linker comprises —NH—R—NH— wherein R is a lower (C1-6) alkylene substituted with a functional group, such as a carboxyl group or an amino group, that enables binding to another molecular moiety (e.g., as may be present on the surface of a solid support during peptide synthesis or to a pharmacokinetic-modifying agent such as PEG). In certain embodiments the linker is a lysine residue. In certain other embodiments, the linker bridges the C-termini of two peptide monomers, by simultaneous attachment to the C-terminal amino acid of each monomer. In other embodiments, the linker bridges the peptides by attaching to the side chains of amino acids not at the C-termini. When the linker attaches to a side chain of an amino acid not at the C-termini of the peptides, the side chain preferably contains an amine, such as those found in lysine, and the linker contains two or more carboxy groups capable of forming an amide bond with the peptides.

The peptide monomers of the disclosure may be oligomerized using the biotin/streptavidin system. Oligomerization can enhance one or more activities of peptides as described herein. Biotinylated analogs of peptide monomers may be synthesized by standard techniques known to those skilled in the art. For example, the peptide monomers may be C-terminally biotinylated. These biotinylated monomers are then oligomerized by incubation with streptavidin (e.g., at a 4:1 molar ratio at room temperature in phosphate buffered saline (PBS) or HEPES-buffered RPMI medium (Invitrogen) for 1 hour). In a variation of this process, biotinylated peptide monomers may be oligomerized by incubation with any one of a number of commercially available anti-biotin antibodies [e.g., goat anti-biotin IgG from Kirkegaard & Perry Laboratories, Inc. (Washington, D.C.)].

In some aspects, the cyclic peptides described herein can be linked physically in tandem to form a polymer. The cyclic peptides making up such a polymer can be spaced apart from each other by a peptide linker. Examples of useful linker peptides include, but are not limited to, glycine polymers ((G)n) including glycine-serine and glycine-alanine polymers (e.g., a (Gly4Ser)n repeat where n=1-8 (SEQ ID NO: 8), preferably, n=3, 4, 5, or 6). The cyclic peptides described herein can also be joined by chemical bond linkages, such as linkages by disulfide bonds or by chemical bridges. Molecular biology techniques that are well known to those skilled in the art can be used to create a polymer of the cyclic peptides. Peptide sequences of the present disclosure can also be linked together using non-peptide cross-linkers (Pierce 2003-2004 Applications Handbook and Catalog, Chapter 6) or other scaffolds such as HPMA, polydextran, polysaccharides, ethylene-glycol, poly-ethylene-glycol, glycerol, sugars, and sugar alcohols (e.g. sorbitol, mannitol).

In some embodiments, polyethylene glycol (PEG) may serve as a linker. In yet another embodiment, a linker moiety may comprise a molecule containing two carboxylic acids and optionally substituted at one or more available atoms with an additional functional group such as an amine capable of being bound to one or more PEG molecules. Such a molecule can be depicted as: —CO—(CH2)n-uX—(CH2)m-CO— where n is an integer between zero and 10, m is an integer between one and 10, X is selected from O, S, N(CH2)pNR1, NCO(CH2)pNR1, and CHNR1, R1 is selected from H, Boc (test-butyloxycarbonyl), Cbz, and p is an integer between 1 and 10. In certain embodiments, one amino group of each of the peptides forms an amide bond with the linker. Optionally, the linker contains one or more reactive amines capable of being derivatized with a suitably activated pharmacokinetic (PK) modifying agent such as a fatty acid, a homing peptide, a transport agent, a cell-penetrating agent, an organ-targeting agent, or a chelating agent.

The cyclic peptide described herein may further comprise one or more water soluble polymer moieties. In some embodiments, these polymers are covalently attached to the cyclic peptide of the disclosure. In some embodiments, for therapeutic use of the end product preparation, the polymer is pharmaceutically acceptable. One skilled in the art will be able to select the desired polymer based on such considerations as whether the polymer-peptide conjugate will be used therapeutically, and if so, the desired dosage, circulation time, resistance to proteolysis, and other considerations. The water soluble polymer may be, for example, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), poly(n-vinyl-pyrrolidone)polyethylene glycol, propropylene glycol homopolymers, polypropylene oxide/ethylene oxide copolymers, and polyoxyethylated polyols. A preferred water soluble polymer is PEG.

The polymer may be of any molecular weight, and may be branched or unbranched. A preferred PEG for use in the present disclosure is linear, unbranched PEG having a molecular weight of from about 5 kilodaltons (kDa) to about 60 kDa (the term "about" indicating that in preparations of PEG, some molecules will weigh more, and some less, than the stated molecular weight). More preferably, the PEG has a molecular weight of from about 10 kDa to about 40 kDa, and even more preferably, the PEG has a molecular weight from 20 to 30 kDa. Other sizes may be used, depending on the desired therapeutic profile (e.g., duration of sustained release desired; effects, if any, on biological activity; ease in handling; degree or lack of antigenicity; and other effects of PEG on a therapeutic peptide known to one skilled in the art).

The number of polymer molecules attached may vary; for example, one, two, three, or more water-soluble polymers may be attached to a peptide of the disclosure. The multiple attached polymers may be the same or different chemical moieties (e.g., PEGs of different molecular weight).

Methods for stabilizing peptides known in the art may be used with the methods and compositions described herein. For example, using D-amino acids, using reduced amide bonds for the peptide backbone, and using non-peptide bonds to link the side chains, including, but not limited to, pyrrolinone and sugar mimetics can each provide stabilization. The design and synthesis of sugar scaffold peptide mimetics are described by Hirschmann et al. (J. Med. Chem., 1996, 36, 2441-2448, which is incorporated herein by reference in its entirety). Further, pyrrolinone-based peptide mimetics present the peptide pharmacophore on a stable background that has improved bioavailability characteristics (see, for example, Smith et al., J. Am. Chem. Soc. 2000, 122, 11037-11038), which is incorporated herein by reference in its entirety.

Encompassed herein are conjugates of the cyclic described herein. These peptides can be conjugated to other polymers in addition to polyethylene glycol (PEG). The polymer may or may not have its own biological activity. Further examples of polymer conjugation include but are not limited to polymers such as polyvinyl pyrrolidone, polyvinyl alcohol, polyamino acids, divinylether maleic anhydride, N-(2-Hydroxypropyl)-methacrylamide, dextran, dextran derivatives including dextran sulfate, polypropylene glycol, polyoxyethylated polyol, heparin, heparin fragments, polysaccharides, cellulose and cellulose derivatives, including methylcellulose and carboxymethyl cellulose, starch and starch derivatives, polyalkylene glycol and derivatives thereof, copolymers of polyalkylene glycols and derivatives thereof, polyvinyl ethyl ethers, and α,β-Poly[(2-hydroxyethyl)-DL-aspartamide, and the like, or mixtures thereof. Conjugation to a polymer can improve serum half-life, among other effects. A variety of chelating agents can be used to conjugate the peptides described herein. These chelating agents include but are not limited to ethylenediaminetetraacetic acid (EDTA), diethylenetriaminepentaacetic acid (DTPA), ethyleneglycol-0,0'-bis(2-aminoethyl)-N,N,N',N'-tetraacetic acid (EGTA), N,N'-bis(hydroxybenzyl)ethylenediamine-N,N'-diacetic acid (HBED), triethylenetetraminehexaacetic acid (TTHA), 1,4,7,10-tetra-azacyclododecane-N,N',N'',N'''-tetraacetic acid (DOTA), 1,4,7,10-tetraazacyclotridecane-1,4,7,10-tetraacetic acid (TITRA), 1,4,8,11-tetraazacyclotetradecane-N,N',N'',N'''-tetraacetic acid (TETA), and 1,4,8,11-tetraazacyclotetradecane (TETRA). Methods of conjugation are well known in the art, for example, P. E. Thorpe, et. al, 1978, Nature 271, 752-755; Harokopakis E., et. al., 1995. Journal of Immunological Methods, 185:31-42; S. F. Atkinson, et. al., 2001, J. Biol. Chem., 276:27930-27935; and U.S. Pat. Nos. 5,601,825, 5,180.816, 6,423,685, 6,706.252, 6,884,780, and 7,022,673, which are hereby incorporated by reference in their entirety.

One can replace the naturally occurring side chains of the genetically encoded amino acids (or the stereoisomeric D amino acids) with other side chains, for instance with groups such as alkyl, lower (C1-6) alkyl, cyclic 4-, 5-, 6-, to 7-membered alkyl, amide, amide lower alkyl amide di(lower alkyl), lower alkoxy, hydroxy, carboxy and the lower ester derivatives thereof, and with 4-, 5-, 6-, to 7-membered heterocycles. In particular, proline analogues in which the ring size of the proline residue is changed from 5 members to 4, 6, or 7 members can be employed. Cyclic groups can be saturated or unsaturated, and if unsaturated, can be aromatic or non-aromatic. Heterocyclic groups preferably contain one or more nitrogen, oxygen, and/or sulfur heteroatoms. Examples of such groups include the furazanyl, furyl, imidazolidinyl, imidazolyl, imidazolinyl, isothiazolyl, isoxazolyl, morpholinyl (e.g. morpholino), oxazolyl, piperazinyl (e.g., 1-piperazinyl), piperidyl (e.g., 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g., 1-pyrrolidinyl), pyrrolinyl, pyrrolyl, thiadiazolyl, thiazolyl, thienyl, thiomorpholinyl (e.g., thiomorpholino), and triazolyl groups. These heterocyclic groups can be substituted or unsubstituted. Where a group is substituted, the substituent can be alkyl, alkoxy, halogen, oxygen, or substituted or unsubstituted phenyl.

One can also readily modify peptides by phosphorylation, and other methods (e.g., as described in Hruby, et al. (1990) Biochem J. 268:249-262).

Treatment

Aspects disclosure relate to methods for treating a subject having cancer. In some embodiments, the method comprises administering to a subject having cancer a cyclic Psap peptide as described herein. In some embodiments, the cyclic peptide comprises the amino acid sequence DWLPK (SEQ ID NO: 1), dWLPK (SEQ ID NO: 3, lower case d indicates D-amino acid), DWGPK (SEQ ID NO: 2), or dWGPK (SEQ ID NO: 4, lower case d indicates D-amino acid). In some embodiments, the amino acid sequence of the cyclic peptide is DWLPK (SEQ ID NO: 1), dWLPK (SEQ ID NO: 3, lower case d indicates D-amino acid), DWGPK (SEQ ID NO: 2), or dWGPK (SEQ ID NO: 4, lower case d indicates D-amino acid). In some embodiments, the cyclic peptide comprises the amino acid sequence DWLPK (SEQ ID NO: 1). In some embodiments, the amino acid sequence of the cyclic peptide is DWLPK (SEQ ID NO: 1).

Other aspects of the disclosure relate to compositions and uses of compositions in the manufacture of a medicament for treating a subject having cancer. In some embodiments, the composition comprises a cyclic Psap peptide as described herein, e.g., a cyclic peptide having the amino acid sequence DWLPK (SEQ ID NO: 1).

As used herein, "treat" or "treatment" of cancer includes, but is not limited to, preventing, reducing, or halting the development of a cancer, reducing or eliminating the symptoms of cancer, suppressing or inhibiting the growth of a cancer, preventing or reducing metastasis and/or invasion of an existing cancer, promoting or inducing regression of the cancer, inhibiting or suppressing the proliferation of cancerous cells, reducing angiogenesis and/or increasing the amount of apoptotic cancer cells.

Yet other aspects of the disclosure relate to methods for treating a subject having an inflammatory disease or disorder. In some embodiments, the inflammatory disease or disorder is inflammatory bowel disease (IBD), e.g., Crohn's disease. In some embodiments, the method comprises administering to a subject having an inflammatory disease or disorder (e.g., Crohn's disease) a cyclic Psap peptide as described herein. In some embodiments, the cyclic peptide comprises the amino acid sequence DWLPK (SEQ ID NO: 1), dWLPK (SEQ ID NO: 3, lower case d indicates D-amino acid), DWGPK (SEQ ID NO: 2), or dWGPK (SEQ ID NO: 4, lower case d indicates D-amino acid). In some embodiments, the amino acid sequence of the cyclic peptide is DWLPK (SEQ ID NO: 1), dWLPK (SEQ ID NO: 3, lower case d indicates D-amino acid), DWGPK (SEQ ID NO: 2), or dWGPK (SEQ ID NO: 4, lower case d indicates D-amino acid). In some embodiments, the cyclic peptide comprises the amino acid sequence DWLPK (SEQ ID NO: 1). In some embodiments, the amino acid sequence of the cyclic peptide is DWLPK (SEQ ID NO: 1).

Other aspects of the disclosure relate to compositions and uses of compositions in the manufacture of a medicament for treating a subject having an inflammatory disease or disorder, e.g., Crohn's disease. In some embodiments, the composition comprises a cyclic Psap peptide as described herein, e.g., a cyclic peptide having the amino acid sequence DWLPK (SEQ ID NO: 1).

As used herein, "treat" or "treatment" of an inflammatory disease or disorder includes, but is not limited to, preventing, reducing or halting the development of an inflammatory disease or disorder or reducing or eliminating the symptoms an inflammatory disease or disorder.

An effective amount is a dosage of the cyclic Psap peptide sufficient to provide a medically desirable result, such as treatment of cancer or an inflammatory disease or disorder. The effective amount will vary with the particular disease or disorder being treated, the age and physical condition of the subject being treated, the severity of the condition, the duration of the treatment, the nature of any concurrent therapy, the specific route of administration and the like factors within the knowledge and expertise of the health practitioner. For administration to a subject such as a human, a dosage of from about 0.001, 0.01, 0.1, or 1 mg/kg up to 50, 100, 150, or 500 mg/kg or more can typically be employed.

In some embodiments, the effective amount is a dosage of the cyclic Psap peptide that causes no toxicity to the subject. In some embodiments, the effective amount is a dosage of the cyclic Psap peptide that causes reduced toxicity to the subject as compared to a linear Psap peptide. As used herein, the term "no toxicity" or "reduced toxicity" indicates that a cyclic Psap peptide does not induce or decreases the incidence or degree of one or more adverse response(s) in a subject or in a cell, tissue or organ of a subject to which it is administered. For example, a cyclic Psap peptide described herein does not cause dysfunction of an organ or a system of organs or cause cell death. For example, a cyclic Psap peptide is not nephrotoxic, not toxic to the spleen and/or not hepatotoxic. Methods for measuring toxicity are well known in the art (e.g., biopsy/histology of the liver, spleen, and/or kidney; alanine transferase, alkaline phosphatase and bilirubin assays for liver toxicity; and creatinine levels for kidney toxicity).

Cyclic Psap peptides and compositions thereof can be formulated for a variety of modes of administration, including systemic, topical or localized administration. A variety of administration routes are available. The particular mode selected will depend upon the type of cancer being treated and the dosage required for therapeutic efficacy. The methods of the disclosure, generally speaking, may be practiced using any mode of administration that is medically acceptable, meaning any mode that produces effective levels of the active compounds without causing clinically unacceptable adverse effects. Such modes of administration include, but are not limited to, oral, rectal, topical, nasal, intradermal, or parenteral routes. The term "parenteral" includes subcutaneous, intravenous, intramuscular, or infusion. The pharmaceutical compositions described herein are also suitably administered by intratumoral, peritumoral, intralesional or perilesional routes, to exert local as well as systemic effects.

Techniques and formulations generally can be found in Remington: The Science and Practice of Pharmacy, Pharmaceutical Press; 22nd edition and other similar references. When administered, a Psap peptide may be applied in pharmaceutically-acceptable amounts and in pharmaceutically-acceptable compositions. Pharmaceutical compositions and pharmaceutically-acceptable carriers are also described herein. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the disclosure. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

In some embodiments, treatment with a cyclic Psap peptide may be combined with another therapy, such as a chemotherapy agent, radiation, a cytostatic agent, an anti-VEGF agent, an anti-angiogenesis factor, a p53 reactivation agent and/or surgery for cancer or an anti-inflammatory agent for an inflammatory disease or disorder.

In some embodiments, a cyclic Psap peptide (e.g., DWLPK (SEQ ID NO: 1) may be used for stimulating expression of Tsp-1 in a subject in need thereof. In some embodiments, a method comprises administering to a subject an effective amount a cyclic Psap peptide to stimulate expression of Tsp-1.

Compositions and Pharmaceutically-Acceptable Carriers

Other aspects of the disclosure relate to compositions comprising a cyclic Psap peptide as described herein. In some embodiments, the composition is a pharmaceutical composition. In some embodiments, the composition comprises a cyclic Psap peptide as described herein and a pharmaceutically-acceptable carrier. In some embodiments, the composition is for use in treating cancer or an inflammatory disease or disorder. In some embodiments, the composition is for use in stimulating Tsp-1 in a subject in need thereof. In some embodiments, the composition comprises an additional agent, e.g., a chemotherapy agent, a cytostatic agent, an anti-VEGF agent, an anti-angiogenesis factor, a p53 reactivation agent and/or an anti-inflammatory agent.

The term "pharmaceutically-acceptable carrier" as used herein means one or more compatible solid or liquid filler, diluents or encapsulating substances which are suitable for administration into a subject, e.g., a human. A pharmaceutically acceptable carrier is "acceptable" in the sense of being compatible with the other ingredients of the formulation and not injurious to the tissue of the patient (e.g., physiologically compatible, sterile, physiologic pH, etc.). The term "carrier" denotes an organic or inorganic ingredient, natural or synthetic, with which the active ingredient is combined to facilitate the application. The components of the pharmaceutical compositions also are capable of being co-mingled with the molecules of the present disclosure, and with each other, in a manner such that there is no interaction which would substantially impair the desired pharmaceutical efficacy. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffeting agents, such as magnesium hydroxide and aluminum hydroxide; (15) alginic acid; (16) pyrogen-free water, (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation.

The pharmaceutical compositions may conveniently be presented in unit dosage form and may be prepared by any of the methods well-known in the art of pharmacy. The term "unit dose" when used in reference to a pharmaceutical composition of the present disclosure refers to physically discrete units suitable as unitary dosage for the subject, each unit containing a predetermined quantity of active material calculated to produce the desired therapeutic effect in association with the required diluent; i.e., carrier, or vehicle.

The formulation of the pharmaceutical composition may dependent upon the route of administration. Injectable preparations suitable for parenteral administration or intratumoral, peritumoral, intralesional or perilesional administration include, for example, sterile injectable aqueous or oleaginous suspensions and may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3 propanediol or 1,3 butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

For topical administration, the pharmaceutical composition can be formulated into ointments, salves, gels, or creams, as is generally known in the art. Topical administration can utilize transdermal delivery systems well known in the art. An example is a dermal patch.

Compositions suitable for oral administration may be presented as discrete units, such as capsules, tablets, lozenges, each containing a predetermined amount of the anti-inflammatory agent. Other compositions include suspensions in aqueous liquids or non-aqueous liquids such as a syrup, elixir or an emulsion.

Other delivery systems can include time-release, delayed release or sustained release delivery systems. Such systems can avoid repeated administrations of the anti-inflammatory agent, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the anti-inflammatory agent is contained in a form within a matrix such as those described in U.S. Pat. Nos. 4,452,775, 4,667,014, 4,748,034 and 5,239,660 and (b) diffusional systems in which an active component permeates at a controlled rate from a polymer such as described in U.S. Pat. Nos. 3,832, 253, and 3,854,480. In addition, pump-based hardware delivery systems can be used, some of which are adapted for implantation.

Use of a long-term sustained release implant may be particularly suitable for treatment of chronic conditions. Long-term release, are used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

In some embodiments, the pharmaceutical compositions used for therapeutic administration must be sterile. Sterility is readily accomplished by filtration through sterile filtration membranes (e.g., 0.2 micron membranes). Alternatively, preservatives can be used to prevent the growth or action of microorganisms. Various preservatives are well known and include, for example, phenol and ascorbic acid. The cyclic Psap peptide and/or the pharmaceutical composition ordinarily will be stored in lyophilized form or as an aqueous solution if it is highly stable to thermal and oxidative denaturation. The pH of the preparations typically will be about from 6 to 8, although higher or lower pH values can also be appropriate in certain instances.

Subjects

Aspects of the disclosure relate to subjects, such as human subjects, having cancer and methods of treating such subjects. The cancer can be benign or malignant, and it may or may not have metastasized. Any type of cancer is contemplated herein, including, but not limited to, leukemias, lymphomas, myelomas, carcinomas, metastatic carcinomas, sarcomas, adenomas, nervous system cancers and genitourinary cancers. Exemplary cancer types include, but are not limited to, adult and pediatric acute lymphoblastic leukemia, acute myeloid leukemia, adrenocortical carcinoma, AIDS-related cancers, anal cancer, cancer of the appendix, astrocytoma, basal cell carcinoma, bile duct cancer, bladder cancer, bone cancer, osteosarcoma, fibrous histiocytoma, brain cancer, brain stem glioma, cerebellar astrocytoma, malignant glioma, ependymoma, medulloblastoma, supratentorial primitive neuroectodermal tumors, hypothalamic glioma, breast cancer, male breast cancer, bronchial adenomas, Burkitt lymphoma, carcinoid tumor, carcinoma of unknown origin, central nervous system lymphoma, cerebellar astrocytoma, malignant glioma, cervical cancer, childhood cancers, chronic lymphocytic leukemia, chronic myelogenous leukemia, chronic myeloproliferative disorders, colorectal cancer, cutaneous T-cell lymphoma, endometrial cancer, ependymoma, esophageal cancer, Ewing family tumors, extracranial germ cell tumor, extragonadal germ cell tumor, extrahepatic bile duct cancer, intraocular melanoma, retinoblastoma, gallbladder cancer, gastric cancer, gastrointestinal stromal tumor, extracranial germ cell tumor, extragonadal germ cell tumor, ovarian germ cell tumor, gestational trophoblastic tumor, glioma, hairy cell leukemia, head and neck cancer, hepatocellular cancer, Hodgkin lymphoma, non-Hodgkin lymphoma, hypopharyngeal cancer, hypothalamic and visual pathway glioma, intraocular melanoma, islet cell tumors, Kaposi sarcoma, kidney cancer, renal cell cancer, laryngeal cancer, lip and oral cavity cancer, small cell lung cancer, non-small cell lung cancer, primary central nervous system lymphoma, Waldenstrom macroglobulinemia, malignant fibrous histiocytoma, medulloblastoma, melanoma, Merkel cell carcinoma, malignant mesothelioma, squamous neck cancer, multiple endocrine neoplasia syndrome, multiple myeloma, mycosis fungoides, myelodysplastic syndromes, myeloproliferative disorders, chronic myeloproliferative disorders, nasal cavity and paranasal sinus cancer, nasopharyngeal cancer, neuroblastoma, oropharyngeal cancer, ovarian cancer, pancreatic cancer, parathyroid cancer, penile cancer, pharyngeal cancer, pheochromocytoma, pineoblastoma and supratentorial primitive neuroectodermal tumors, pituitary cancer, plasma cell neoplasms, pleuropulmonary blastoma, prostate cancer, rectal cancer, rhabdomyosarcoma, salivary gland cancer, soft tissue sarcoma, uterine sarcoma, Sezary syndrome, non-melanoma skin cancer, small intestine cancer, squamous cell carcinoma, squamous neck cancer, supratentorial primitive neuroectodermal tumors, testicular cancer, throat cancer, thymoma and thymic carcinoma, thyroid cancer, transitional cell cancer, trophoblastic tumors, urethral cancer, uterine cancer, uterine sarcoma, vaginal cancer, vulvar cancer, or Wilms tumor. In some embodiments, the cancer is melanoma or ovarian cancer.

Subjects having cancer may be identified using any method known in the art (e.g., blood tests, histology, CT scan, X-ray, MRI, physical exam, cytogenitic analysis, urinalysis, or genetic testing). A subject suspected of having cancer might show one or more symptoms of the disease. Signs and symptoms for cancer are well known to those of ordinary skill in the art. Some exemplary laboratory tests include, but are not limited to, testing for cancer biomarkers such as cancer antigen (CA) 15-3, carcinoembryonic antigen (CEA) and HER-2 for breast cancer, human papillomavirus (HPV) E6 and E7 oncoproteins for cervical cancer, alpha-fetoprotein (AFP), AFP fractions L3, P4/5, and the +II band, and ultrasonography for hepatocellular carcinoma (HCC), prostate-specific antigen (PSA) for prostate cancer, and serum CA-125 for ovarian and HCC.

Other aspects of the disclosure relate to subjects, such as human subjects, having inflammatory diseases or disorders and methods of treating such subjects. Exemplary inflammatory diseases or disorders include, but are not limited to, rheumatoid arthritis, macular degeneration (e.g., age-related macular degeneration, AMD), inflammatory bowel disease (IBD, e.g., Crohn's disease or ulcerative colitis), psoriasis, atherosclerosis, systemic lupus erythematosus, alopecia areata, anklosing spondylitis, antiphospholipid syndrome, autoimmune Addison's disease, autoimmune hemolytic anemia, autoimmune hepatitis, autoimmune inner ear disease, autoimmune lymphoproliferative syndrome (ALPS), autoimmune thrombocytopenic purpura (ATP), Behcet's disease, bullous pemphigoid, cardiomyopathy, celiac sprue-dermatitis, chronic fatigue syndrome immune deficiency syndrome (CFIDS), chronic inflammatory demyelinating polyneuropathy, cicatricial pemphigoid, cold agglutinin disease, Crest syndrome, Dego's disease, dermatomyositis, dermatomyositis-juvenile, discoid lupus, essential mixed cryoglobulinemia, fibromyalgia-fibromyositis, grave's disease, guillain-barre, hashimoto's thyroiditis, idiopathic pulmonary fibrosis, idiopathic thrombocytopenia purpura (ITP), Iga nephropathy, insulin dependent diabetes (Type I), juvenile arthritis, Meniere's disease, mixed connective tissue disease, multiple sclerosis, myasthenia gravis, pemphigus vulgaris, pernicious anemia, polyarteritis nodosa, polychondritis, polyglancular syndromes, polymyalgia rheumatica, polymyositis and dermatomyositis, primary agammaglobulinemia, primary biliary cirrhosis, Raynaud's phenomenon, Reiter's syndrome, rheumatic fever, sarcoidosis, scleroderma, Sjogren's syndrome, stiff-man syndrome, Takayasu arteritis, temporal arteritis/giant cell arteritis, uveitis, vasculitis, vitiligo, and Wegener's granulomatosis. In some embodiments, the inflammatory disease or disorder is rheumatoid arthritis, macular degeneration (e.g., age-related macular degeneration, AMD), inflammatory bowel disease (IBD, e.g., Crohn's disease or ulcerative colitis), psoriasis, or atherosclerosis.

Subjects having an inflammatory disease or disorder may be identified using any method known in the art (e.g., blood tests, physical exam, CT scan, or MRI). A subject suspected of having an inflammatory disease or disorder might show one or more symptoms of the disease or disorder. Signs and symptoms for inflammatory diseases or disorders are well known to those of ordinary skill in the art.

In some embodiments, the inflammatory disease or disorder is inflammatory bowel disease (IBD), e.g., Crohn's disease. Subjects having IBD, e.g., Crohn's disease, may be identified using any method known in the art (e.g., blood tests, physical exam, fecal occult blood test, colonoscopy, flexible sigmoidoscopy, CT scan, MRI, capsule endoscopy, double balloon endoscopy, small bowel imaging, or a barium enema). A subject suspected of having IBD might show one or more symptoms of the disease. Signs and symptoms for IBD are well known to those of ordinary skill in the art.

EXAMPLES

Example 1

Cyclic versions of the peptides DWLPK (SEQ ID NO: 1), dWLPK (SEQ ID NO: 3), DWGPK (SEQ ID NO: 2), and dWGPK (SEQ ID NO: 4) were synthesized according to methods known in the art (lower case d indicates a D-amino acid) and compared to a linear peptide dWlP (SEQ ID NO: 5, lower case d and l indicate D-amino acids).

Figure 2:
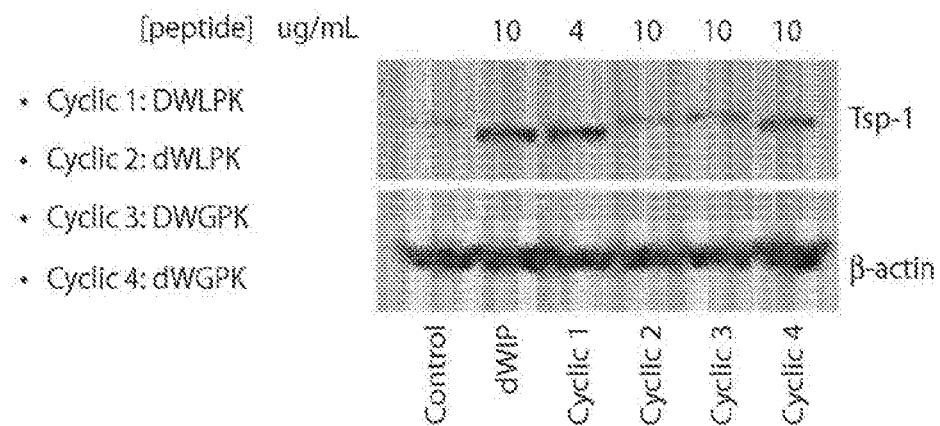
FIG. 2 is a photograph of a Western blot showing the level of thrombospondin-1 (Tsp-1) activation in cells in response to different cyclic or linear peptides (SEQ ID NOs: 1, 3, 2 and 4, respectively from top to bottom).

Cells were cultured and contacted with 4 micrograms/mL or 10 micrograms/mL of each peptide and the level of thrombospondin-1 (Tsp-1) activation was measured by Western blot. Tsp-1 has been previously shown to be activated by Saposin A protein. FIG. 2 shows that the cyclic peptide DWLPK (SEQ ID NO: 1) was the most effective at increasing the level of Tsp-1, with dWGPK (SEQ ID NO: 4) being the next most effective and dWLPK (SEQ ID NO: 3) and DWGPK (SEQ ID NO: 2) being the least effective. This was surprising, as a similar study with linear versions of these peptides revealed that linear DWGPK (SEQ ID NO: 2) was more effective than linear DWLPK (SEQ ID NO: 1).

Figure 3:
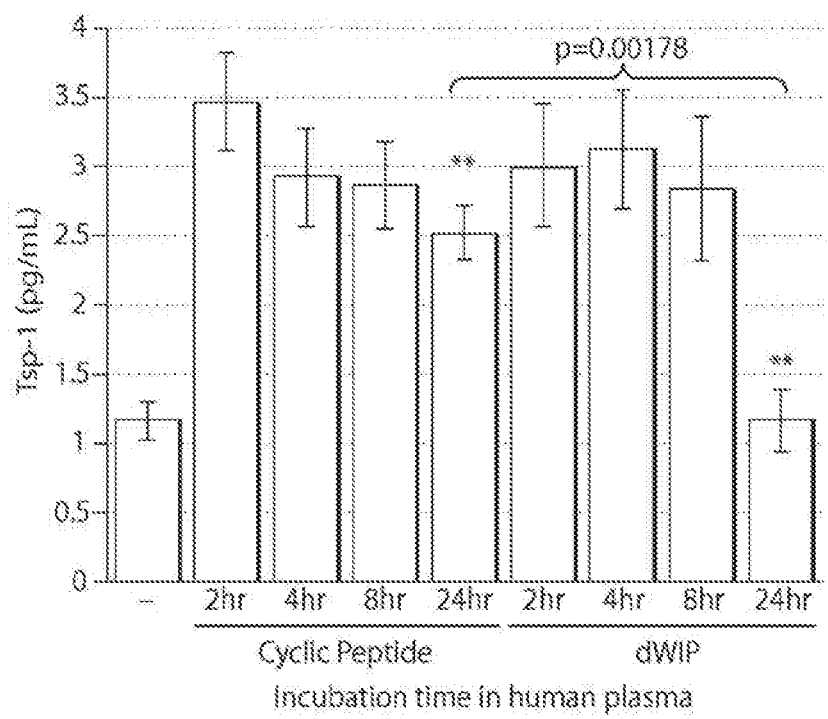
FIG. 3 is a graph showing the ability of cyclic DWLPK (SEQ ID NO: 1) or linear dWlP SEQ ID NO: 5) to activate Tsp-1 after incubation in human plasma.

The cyclic peptide DWLPK (SEQ ID NO: 1) was also tested for stability in human plasma compared to the linear peptide dWlP (SEQ ID NO: 5). Each peptide was incubated in human plasma at 37 degrees Celsius, for 2, 4, 8, or 24 hours. It was found that the cyclic peptide retained the ability to activate Tsp-1, even after 24 hours of incubation in the plasma (FIG. 3). The linear peptide had significantly less activity at 24 hours, despite being stabilized against degradation by D-amino acid substitutions.

Figure 4:
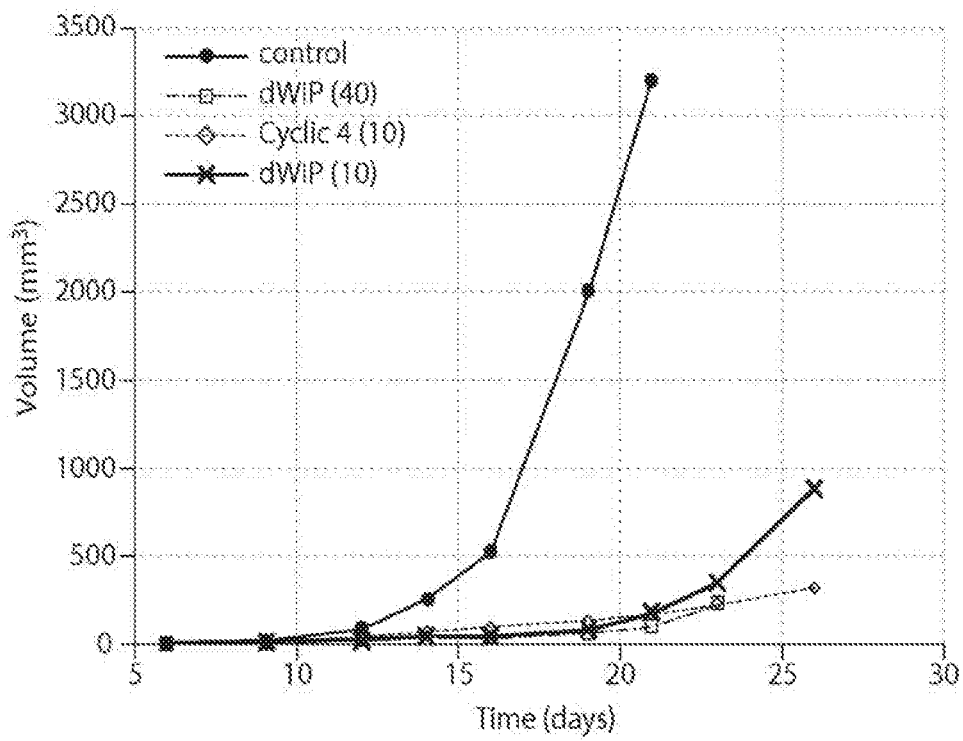
FIG. 4 is a graph showing the tumor volume in mice treated with a cyclic peptide or a linear peptide.
Figure 5:
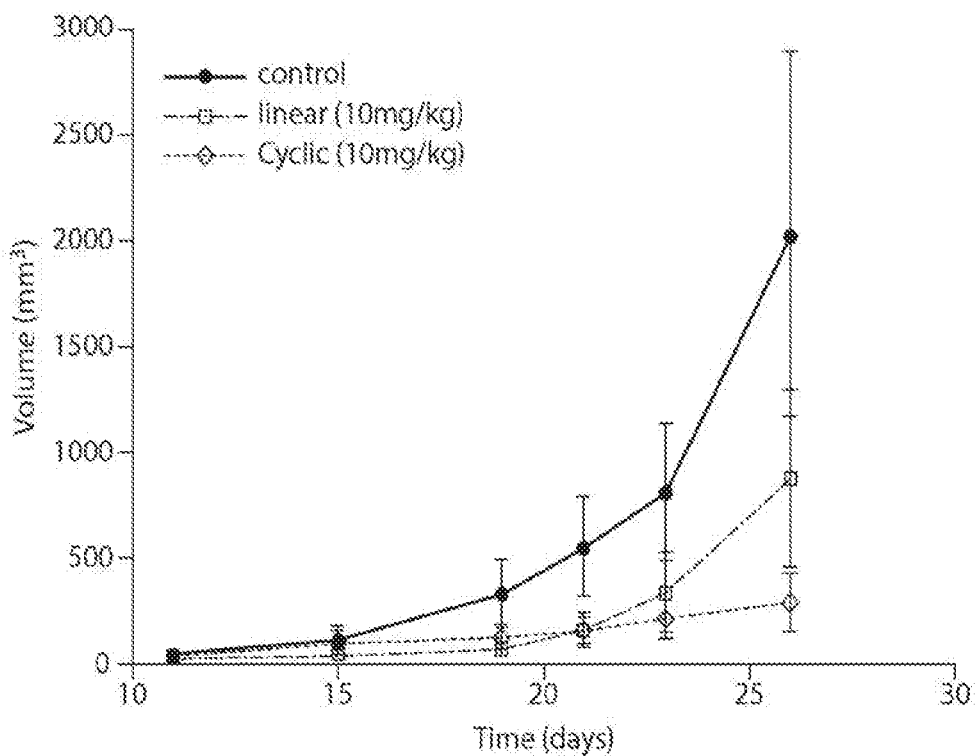
FIG. 5 is a graph showing the tumor volume in mice treated with a cyclic peptide or a linear peptide.

The cyclic peptide dWGPK (SEQ ID NO: 4) was then tested in a mouse model of melanoma. For the melanoma model, $5 \times 10^5$ Bl6-Bl6 melanoma cells were injected in syngeneic C57Bl6 mice. Mice were then treated with either the cyclic peptide or linear dWlP (SEQ ID NO: 5) or control. In a first experiment, treatment with the peptides began about day 12 and the volume of the tumor was measured over time up until about 20-25 days post cell injection (FIG. 4). In a second experiment, treatment with the peptides began on day 15 and the volume of the tumor was measured over time up until about 27 days post cell injection (FIG. 5). It was found that the cyclic peptide was four times as effective as the linear peptide, as a dose of 10 mg/kg of the cyclic peptide was as effective as a dose of 40 mg/kg of the linear peptide (FIG. 4). This was confirmed in the second experiment (FIG. 5).

Figure 6:
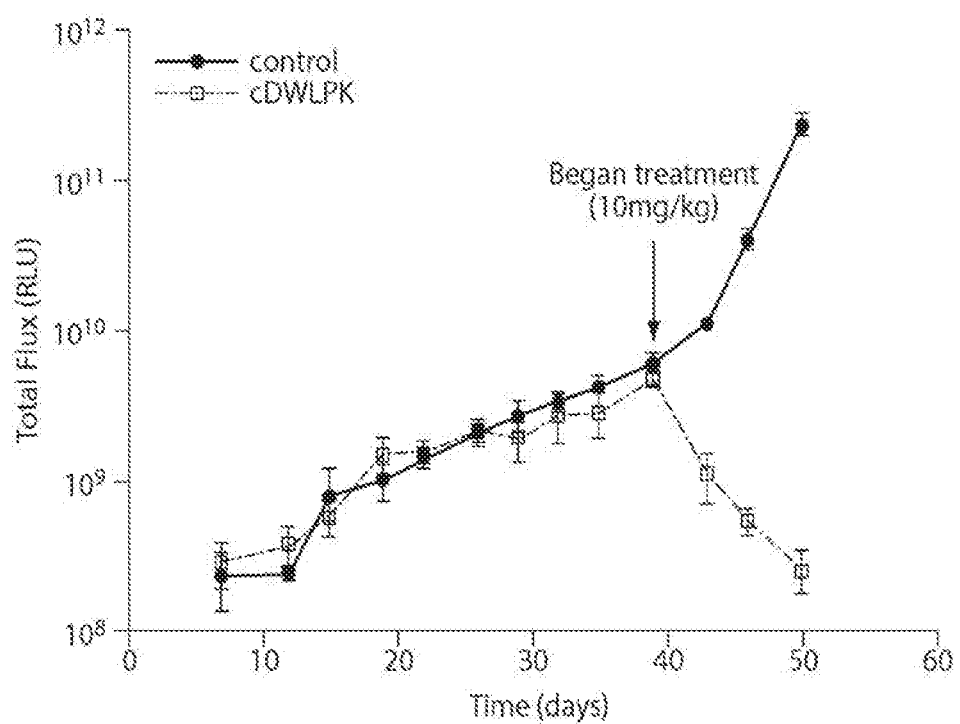
FIG. 6 is a graph showing the total flux of luciferase-expressing tumor cells injected into mice after treatment with a cyclic peptide or control.

Next the cyclic peptide DWLPK (SEQ ID NO: 1) was tested in a mouse model of ovarian cancer. For the ovarian cancer mouse model. 1 million patient-derived ovarian cancer cells expressing luciferase were injected intraperitoneally into mice. The tumor burden was measured in vivo using luciferase. Treatment with the cyclic peptide began after 40 days and was administered for 10 days at 10 mg/kg. After 10 days of treatment, the mice were euthanized and the tumor was analyzed histologically. As shown in FIG. 6, the luciferase output in mice treated with the cyclic peptide went down over the 10 days of treatment, indicated regression of the tumor. All cyclic peptide treated tumors expressed Tsp-1 and were <25% the size of untreated tumors upon observation by histology.

Figure 7:
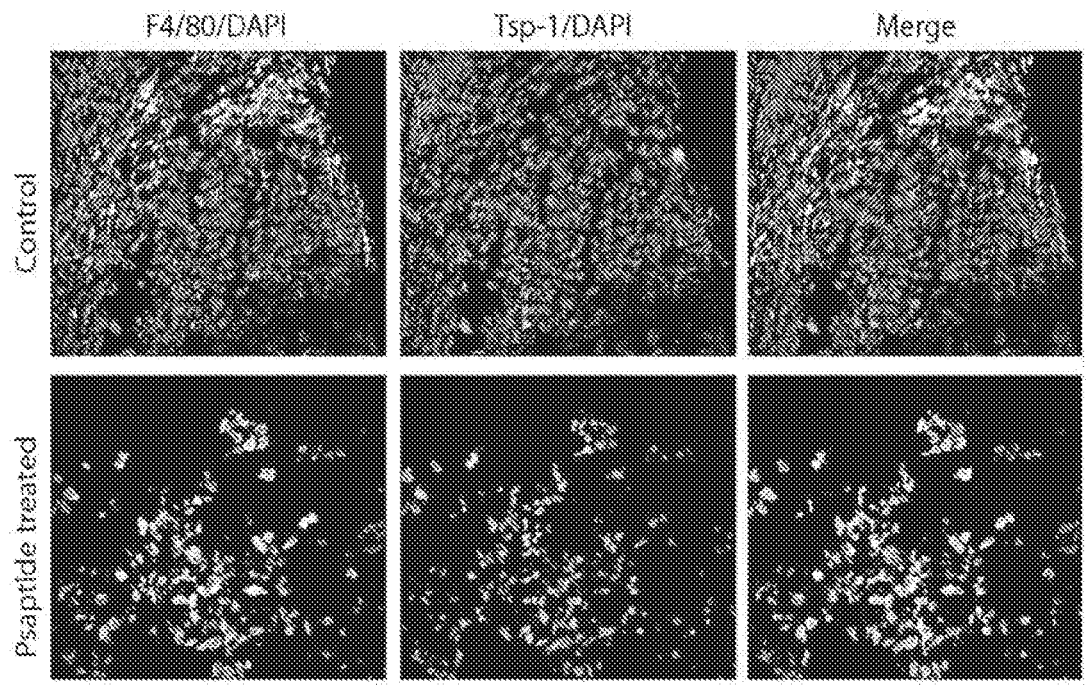
FIG. 7 is a series of photographs showing that Tsp-1 is expressed in macrophages that express F4/80.

It was also shown that the cyclic peptide DWLPK (SEQ ID NO: 1) stimulated Tsp-1 in macrophages in mice (FIG. 7), indicating that the cyclic peptide could also induce expression of Tsp-1 in the stroma.

Figure 8:
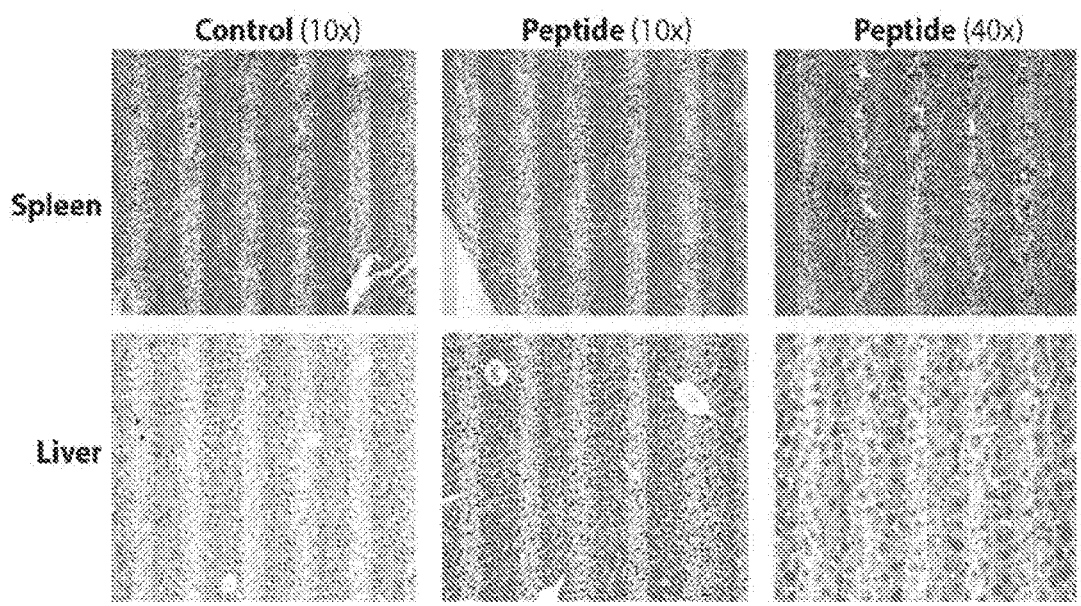
FIG. 8 is a series of photographs showing the histology of liver and spleen samples in mice injected with control or cyclic DWLPK (SEQ ID NO: 1).

Lastly, it was shown that dosage with the cyclic peptide DWLPK (SEQ ID NO: 1) did not cause any toxicity to the liver or spleen, as measured using histology (FIG. 8).

In summary, these data show that cyclic Psap peptides were more stable and more effective than linear Psap peptides. In addition, the cyclic peptide DWLPK (SEQ ID NO: 1) appeared to have the best activity in vitro and did not induce toxicity.

Example 2

Figure 9:
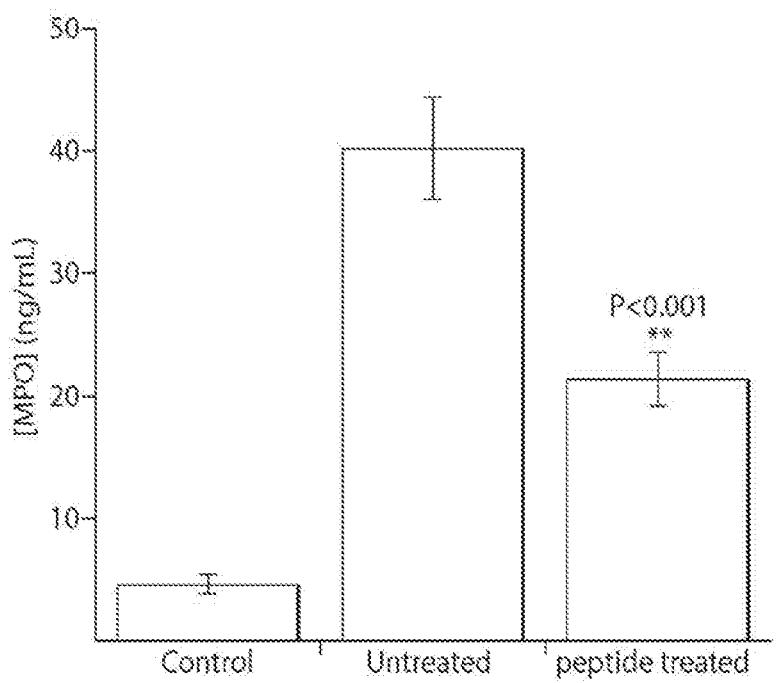
FIG. 9 is a graph showing the MPO enzymatic activity (an index of neutrophil infiltration into the colonic mucosa) in a Dextran Sodium Sulfate (DSS)-induced mouse model of Crohn's disease treated with control, untreated, or treated with cyclic DWLPK (SEQ ID NO: 1).
Figure 10:
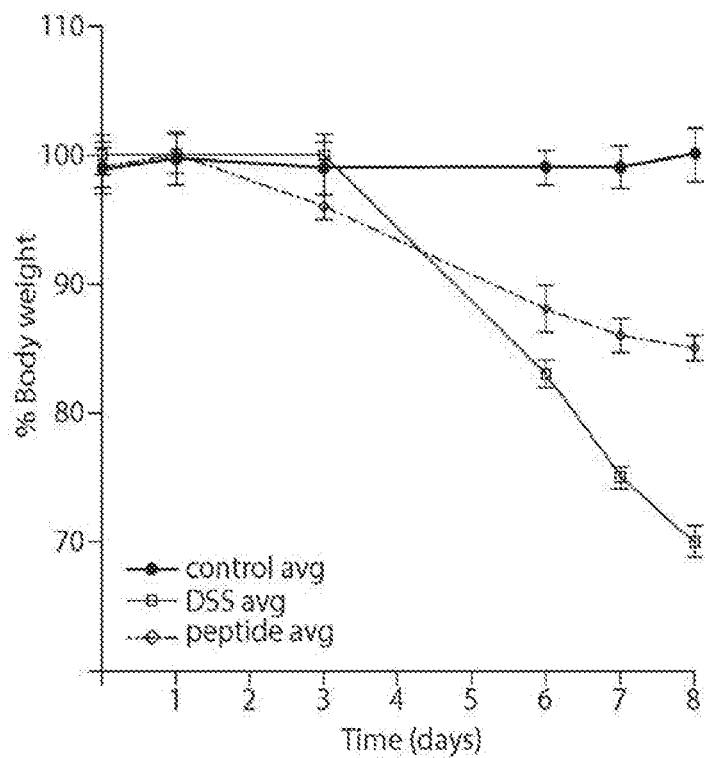
FIG. 10 is a graph showing the percent body weight in a mouse model of Crohn's disease treated with control, untreated, or treated with cyclic DWLPK (SEQ ID NO: 1).
Figure 11:
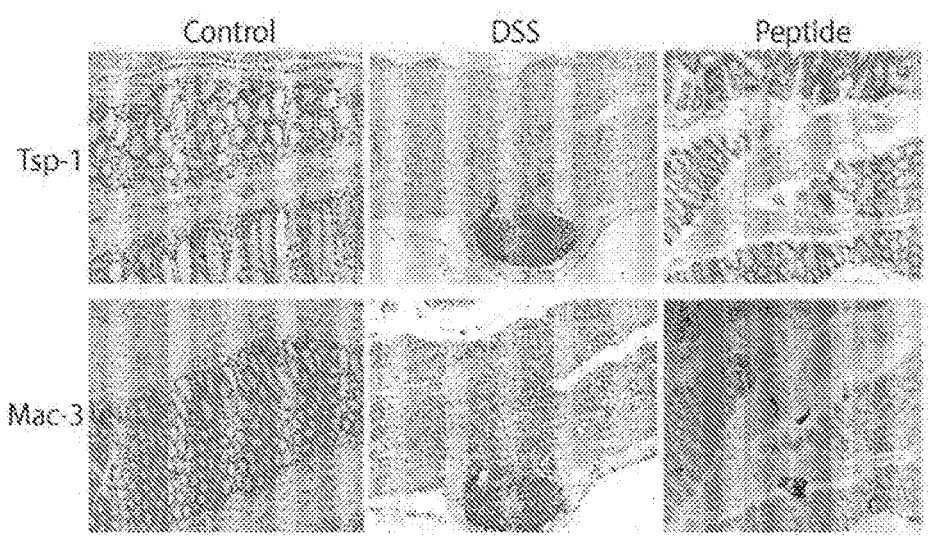
FIG. 11 is a series of photographs showing the histology of the intestine and macrophage localization in a mouse model of Crohn's disease treated with control, untreated, or treated with cyclic DWLPK (SEQ ID NO: 1).

A model of Crohn's disease was used to test the efficacy of the cyclic peptide DWLPK (SEQ ID NO: 1) for treating Crohn's disease. The cyclic peptide was tested in a Dextran Sodium Sulfate (DSS)-induced model of Crohn's Disease where DSS was given to the mice in their drinking water (3.5% weight:volume) for 7 days. In one group the mice were treated concurrently with the cyclic peptide and DSS, while the other group was treated with DSS alone. The cyclic peptide significantly reduced inflammation in this model (FIG. 9). The mice treated with cyclic peptide also lost less weight than the mice treated with only DSS (FIG. 10). Lastly, the cyclic peptide was shown to stimulate Tsp-1 and inhibit macrophage infiltration in these mice (FIG. 11). These data suggest that cyclic Psap peptides, in particular cyclic DWLPK (SEQ ID NO: 1), are effective for treating Crohn's disease.

Example 3

(i) A model of AMD is used to test the efficacy of a cyclic Psap peptide described herein in treating AMD. Lesions are created on a mouse's retina with a laser. The mice are then treated with cyclic Psap peptide as described herein, e.g., 10 or 40 mg/kg of cyclic DWLPK (SEQ ID NO: 1), or a scrambled peptide control. Treatment is either systemically (e.g., by intravenous or intraperitoneal injection) or by intravitreous injection. The rate of healing of the lesion is measured over time. It is expected that the lesion will heal faster in mice treated with the cyclic Psap peptide than in mice treated with the control.

(ii) A rodent model of collagen induced arthritis (CIA), an autoimmune model that resembles rheumatoid arthritis, is used to test the efficacy of a cyclic Psap peptide described herein for treating rheumatoid arthritis. CIA is inducible in inbred DBA/1 male mice by priming intradermally with heterologous or homologous collagen II (about 50 microgram) in Freunds complete adjuvant and 2 weeks later boosting with the same amount of collagen II in Freunds incomplete adjuvant. The arthritis develops approximately 3 weeks after the priming dose and reaches its maximum within 8 weeks post priming. The mice have high levels of collagen II specific antibodies, collagen II specific T cells as well as signs of systemic inflammation (e.g. production of IL-6, TNF etc.). Locally in the joints one observes both overwhelming inflammatory infiltrates (consisting of T cells, macrophages, neutrophils and fibroblasts) as well as severe destruction of cartilage and subchondral bone. These features mimic well the process seen in human rheumatoid arthritis (Myers et al., Life Sciences 61, p 1861-1878, 1997). The mice are then treated with cyclic Psap peptide as described herein, e.g., 10 or 40 mg/kg of cyclic DWLPK (SEQ ID NO: 1), or a scrambled peptide control. Treatment is either systemically (e.g., by intravenous or intraperitoneal injection) or by local administration. Several parameters of the disease (e.g., clinical signs and symptoms, onset, progression, severity, and remission of symptoms) are measured. It is expected that one or more of these parameters will be improved (e.g., decreased clinical signs and symptoms, delayed onset, slowed progression, reduced severity, and/or remission) in mice treated with the cyclic Psap peptide than in mice treated with the control.

(iii) A model of psoriasis is used to test the efficacy of a cyclic Psap peptide described herein in treating psoriasis. Imiquimod (IMQ) is applied to the skin of mice to induce psoriasis-like dermatitis (see, e.g., van der Fits et al. Imiquimod-induced psoriasis-like skin inflammation in mice is mediated via the IL-23/IL-17 axis, (2009) J. Immunol.; 182(9):5836-45). The mice are then treated with cyclic Psap peptide as described herein, e.g., 10 or 40 mg/kg of cyclic DWLPK (SEQ ID NO: 1), or a scrambled peptide control. Treatment is either systemically (e.g., by intravenous or intraperitoneal injection) or topically. The rate of healing of the dermatitis is measured over time. Epidermal expression of IL-23, IL-17A, and IL-17F is also measured at the conclusion of the experiment. It is expected that the dermatitis will heal faster and the levels of IL-23, IL17A, and/or IL17F will be decreased in mice treated with the cyclic Psap peptide compared to mice treated with the control.

(iv) A model of atherosclerosis is used to test the efficacy of a cyclic Psap peptide described herein in treating atherosclerosis. Mice lacking the apoE or the LDL receptor (LDLR) gene are used as a model for atherosclerosis. The mice are fed a high-fat, high-cholesterol Western type diet or regular chow for 8 weeks or more, preferably at least 15 weeks. The mice are treated with cyclic Psap peptide as described herein, e.g., 10 or 40 mg/kg of cyclic DWLPK (SEQ ID NO: 1), or a scrambled peptide control. Treatment is systemically delivered (e.g., by intravenous or intraperitoneal injection). Lesions that develop in the aortic root, the innominate artery (brachiocephalic) and other branches of the aorta, as well as the pulmonary and carotid arteries are measured in the mice after at least 8 weeks. It is expected that the lesions will heal faster in mice treated with the cyclic Psap peptide than in mice treated with the control.

Example 4

Abstract

Virtually 100% of ovarian cancer-related deaths are caused by metastatic dissemination of cells from the primary tumor resulting in subsequent organ failure. However, despite the increased understanding into the physiological processes involved in tumor metastasis, there are no clinically approved drugs that have shown significant efficacy at treating advanced, metastatic, ovarian cancer. Psap has been identified as a potent inhibitor of tumor metastasis via stimulation of p53 and the anti-tumorigenic protein thrombospondin-1 (Tsp-1) in bone marrow derived cells that are recruited to metastatic sites. It is demonstrated that ~100% of human serous ovarian tumors express CD36, the receptor that mediates the pro-apoptotic activity of Tsp-1. A peptide derived from Psap which would be effective in treating this form of ovarian cancer was investigated. The activity and stability of the peptide was investigated by developing a novel cyclic peptide with drug-like properties derived from Psap. The cyclic Psap peptide was able to significantly regress a PDX model of metastatic ovarian cancer.

Introduction

Ovarian cancer is the most lethal gynecologic malignancy and the fourth leading cause of cancer deaths in women. Pathologically, ovarian cancer is categorized into multiple subtypes, with epithelial ovarian cancer (EOC) representing 90% of cases. Despite our increased understanding of the biology governing the progression of EOC the survival rate for patients with stage IV EOC is only 17%. As such, there is a need for efficacious therapies that can specifically treat advanced, metastatic ovarian cancer. While many patients display a response to platinum agents as first line therapies, 70% percent develop resistance (1, 2). Currently for these patients there are no approved therapies that significantly increase overall survival.

It has been previously reported that the development of a small peptide derived from Psap potently inhibits tumor metastasis in multiple types of tumor models (3, 4). Specifically. Psap, and the peptide derived from it, inhibits tumor metastasis by stimulating the broadly acting anti-tumorigenic protein Thrombospondin-1 (Tsp-1) in CD11b$^+$/Gr1$^+$/Lys6C$^{hi}$ monocytes (3). These monocytes are recruited to sites of future metastatic lesions, termed premetastatic niches, where they persist after colonization and stimulate tumor growth. However, systemic administration of the Psap peptide stimulates the production of Tsp-1 in these cells, which renders the sites refractory to future metastatic colonization (3). These results demonstrate that stimulation of Tsp-1 in the tumor microenvironment could prevent future metastatic events. Many ovarian cancer patients present at first diagnosis with metastatic disease. As such, a therapeutic agent that can regress, or even stabilize, metastatic lesions is needed.

It is demonstrated that stimulating Tsp-1 in the microenvironment of a metastatic, platinum resistant, ovarian cancer PDX model can induce significant regression of established lesions. Such a striking effect is achieved due to the fact that serous ovarian cancer cells express the receptor for Tsp-1, CD36, that mediates the proapoptotic effect previously observed in endothelial cells (5).

Results

Incorporation of d-Amino Acids Increases the Activity of a Psap Peptide In Vivo

Figure 12A:
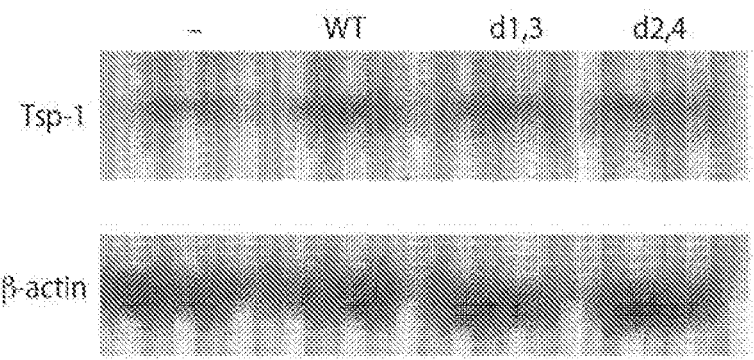
FIGS. 12A-12E show stimulation of Tsp-1 and its effects on ovarian cancer cell growth and survival.

Identification of both a 4- and 5-amino acid peptide derived from the saposin A domain of Psap that was able to inhibit both a tail vein model of Lewis Lung Carcinoma metastasis and in an adjuvant model of breast cancer metastasis when administered systemically was previously described (3). The therapeutic efficacy of peptides is often limited by their stability, or resistance to degradation by proteases. One common method of increasing the stability of peptides in vivo is to incorporate d-amino acids into the sequence, since d-amino acids are not incorporated into naturally occurring proteins, proteases do not recognize them as substrates (6-10). The stability of the 4-amino acid Psap peptide by incorporating d-amino acids at different moieties was investigated. Two peptides with d-amino acids incorporated, in combination, at the first (aspartate) and third (leucine) or the second (tryptophan) and fourth (proline) residues were synthesized. The activity of these peptides along with the native l-amino acid peptide in vitro by measuring their ability to stimulate thrombospondin-1 (Tsp-1) in WI-38 lung fibroblasts was tested. By western blot analysis, it was found that there was no difference in the stimulation of Tsp-1 between the three peptides in vitro (FIG. 12A).

Figure 12B:
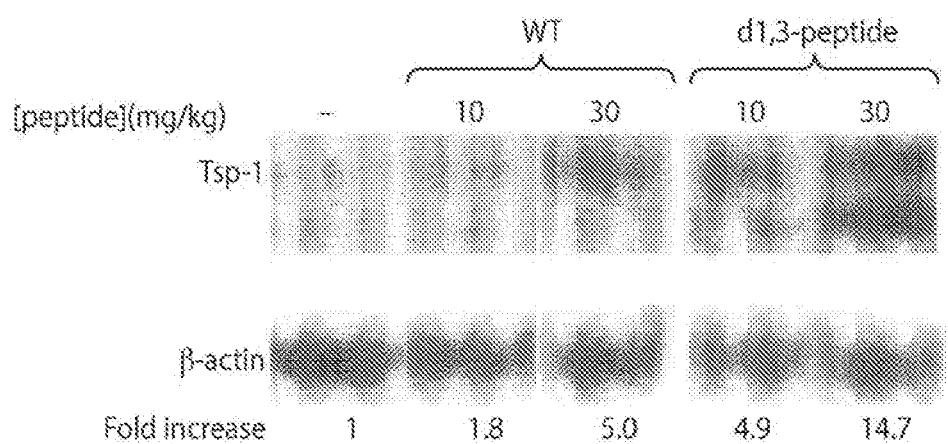

The activity of the 1,3-d-amino acid Psap peptide and the native Psap peptide were tested in vivo. The peptides were systematically administered to C57BL6/J mice that were pretreated with conditioned media (CM) from PC3M-LN4 (LN4) cells, which previously mimicked the systemic properties of metastatic tumors by repressing the expression of Tsp-1 in the lungs of mice (3, 4). After 3 days of treatment with LN4 CM alone or in combination with two different doses (10 mg/kg/day and 30 mg/kg/day) of d- and l-amino acid peptides (independently) protein pools were prepared from the harvested lungs of each treatment group. The level of Tsp-1 expression in the lungs of these mice were assessed by western blot analysis. It was observed that the 1,3-d-amino acid peptide stimulated Tsp-1 3-fold greater than the native peptide (FIG. 12B). A dose of 10 mg/kg of the native peptide did not significantly stimulate Tsp-1 (FIG. 12B). Conversely, a dose of 10 mg/kg of the d-amino acid peptide stimulated Tsp-1 to the same degree as a dose of 30 mg/kg of the native peptide and a dose of 30 mg/kg of the d-amino acid peptide stimulated Tsp-1 approximately 3-fold greater than the same dose of native peptide. Based on the observation that the in vitro activity of the two peptides was virtually identical, it was concluded that the difference in activity in vivo was due to a difference in stability.

Human Serous Ovarian Cancer Cells are Sensitive to Tsp-1 Mediated Killing

Figure 12C:
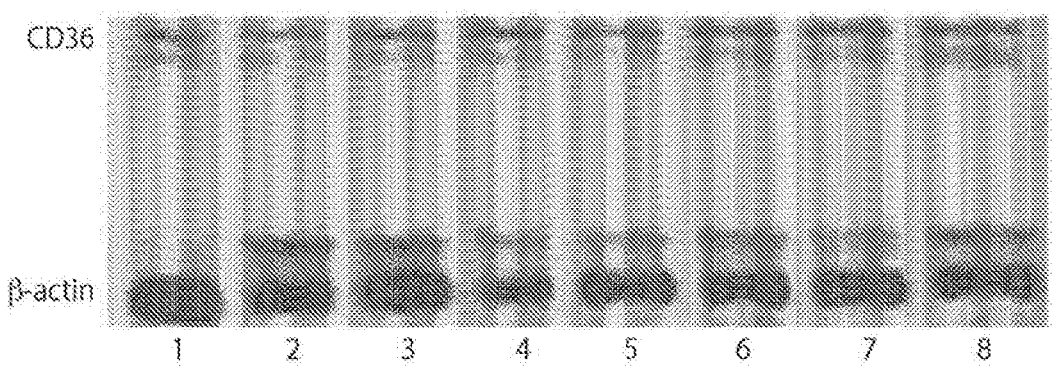
Figure 12D:
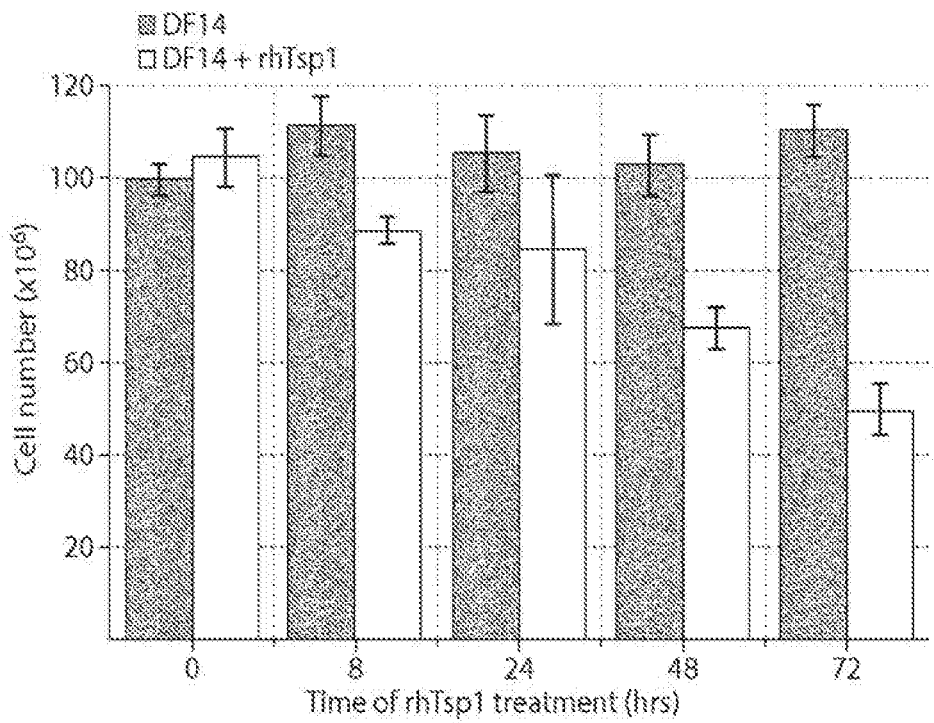
Figure 12E:
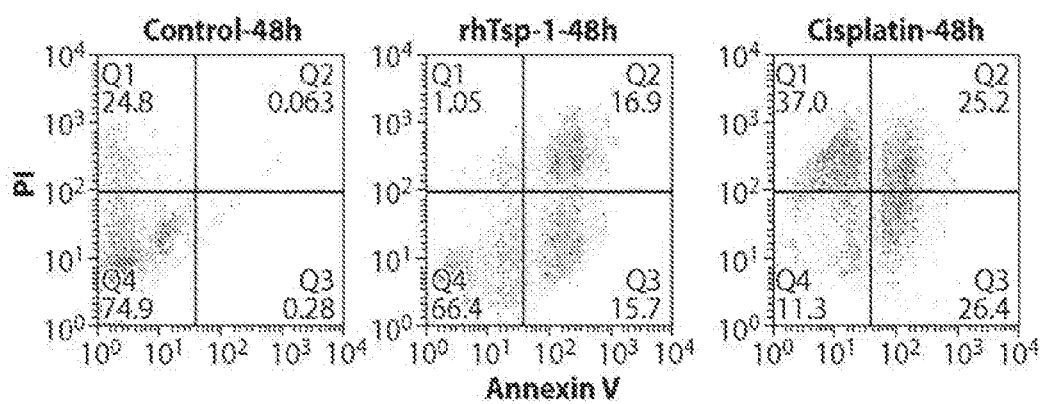

In order to test the efficacy of the d-amino acid Psap peptide, a suitable tumor model that would represent a potential clinical application for the peptide, was determined. Given that Psap, and the peptide derived from it, stimulates Tsp-1 in bone marrow derived cells that are recruited to sites of metastasis, a specific type of cancer that expressed the receptor for Tsp-1 that mediates its pro-apoptotic activity, CD36 was sought to be identified (5). It has been reported that serous ovarian epithelial cells and human ovarian cancer cells express CD36 (11-13). Fourteen primary human ovarian cancer cell lines derived from the ascites of patients with platinum resistant ovarian cancer for expression of CD36 were surveyed. All of the patient derived cells expressed levels of CD36 that were approximately equivalent to the level expressed by human microvascular endothelial cells (FIG. 12C). Three of these cell lines were treated with recombinant human Tsp-1 for up to 72 hours and determined its effect on cell number and apoptosis. RhTsp-1 treatment resulted in a decrease in total cell number for all three cell lines of up to 50% of the original number of cells plated (FIG. 12D). Moreover, by FACS analysis 30-60% of treated cells were observed to be apoptotic following Tsp-1 treatment, as defined by Anexin V positivity (FIG. 12E). In contrast, it was observed that following cisplatin treatment a much greater percentage of ovarian cancer cells underwent necrosis, as defined by low Anexin V and high propidium iodide (PI) staining (FIG. 12E). These findings suggest that ovarian cancer cells may respond favorably to treatment with the Psap peptide.

Figure 13A:
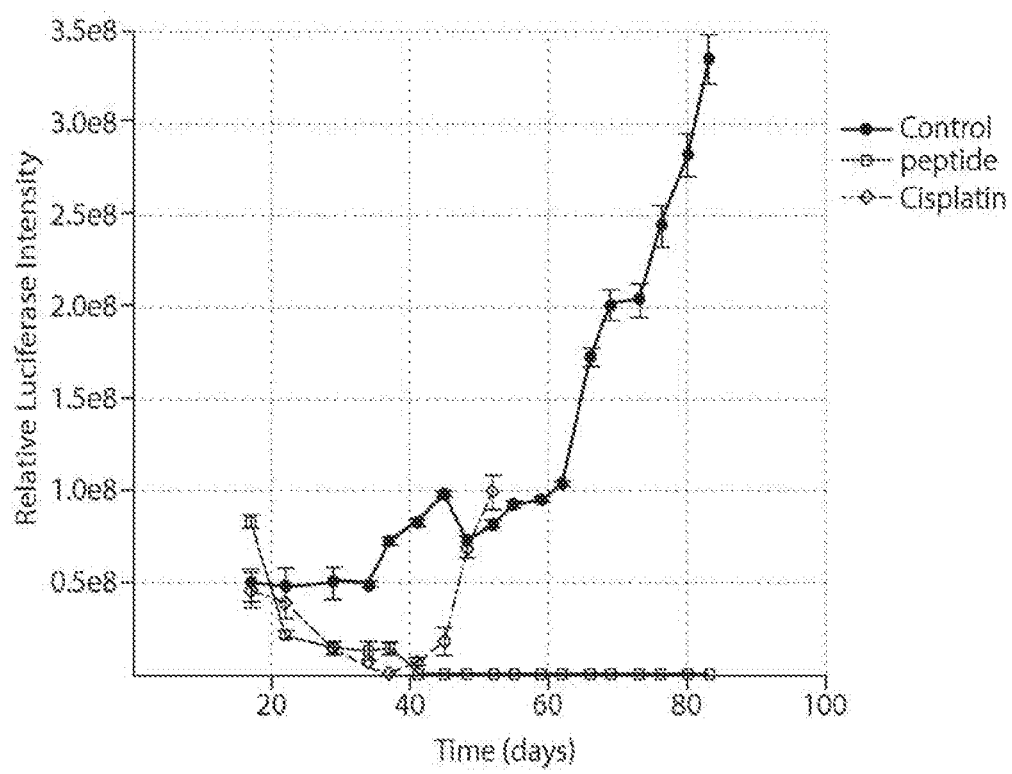
FIGS. 13A-13E show the effects of a d-amino acid prosaposin peptide on a PDX model of metastatic ovarian cancer.
Figure 13B:
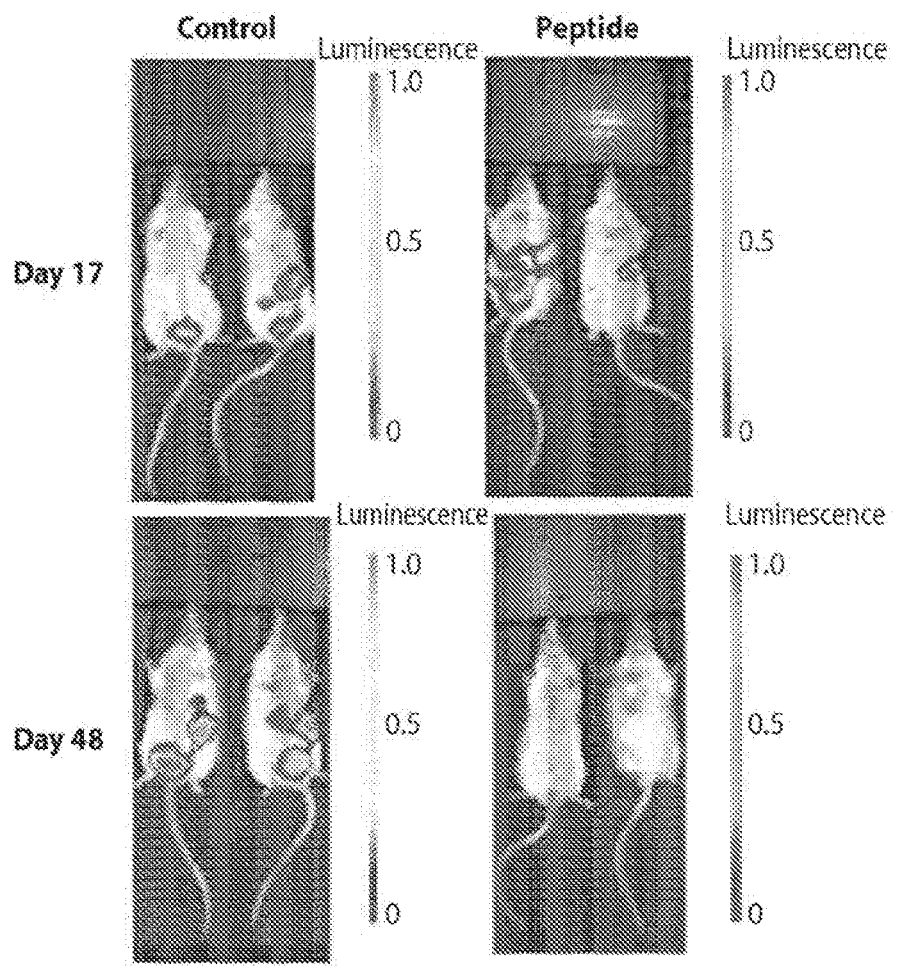
Figure 13C:
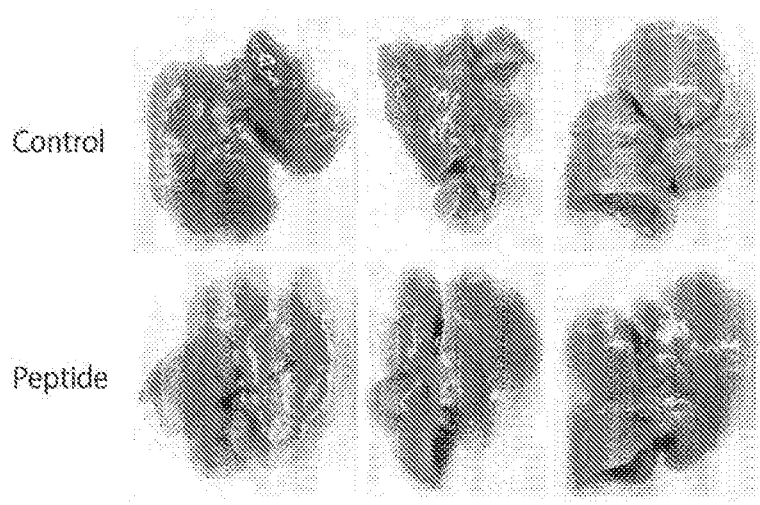

The Psap Peptide Regresses an Established PDX Model of Ovarian Cancer Metastases It was previously demonstrated that Psap and the Psap peptide could inhibit the formation of metastases (3, 4). 75 percent of ovarian cancer patients already have disseminated disease at the time of first diagnosis (E. Lengyel, Ovarian cancer development and metastasis, Am J Pathol 177, 1053-1064 (2010)). For these patients inhibiting metastasis would have limited therapeutic benefit. Rather, these patients require a therapeutic agent that can regress or, at the very least, stabilize existing metastases. Whether the d-amino acid Psap peptide could have therapeutic efficacy in a model of established metastatic dissemination was investigated. $1 \times 10^6$ DF14 cells, expressing firefly luciferase, were injected into the peritoneal cavity of SCID mice to mimic the route of dissemination of human ovarian cancer. The growth of metastatic colonies in the mice in real time were monitored via relative luciferase intensity and when the average intensity of the luciferase signal was $0.5-1 \times 10^8$ RLU, treatment with vehicle (saline), the d-amino acid peptide (40 mg/kg QD), or cisplatin (4 mg/kg QOD) was started. Both the peptide and cisplatin were able to regress tumor volume, as determined by luciferase intensity, for the first 20 days of treatment (FIGS. 13A and 13B). However, during those 20 days half of the cisplatin treated mice died from adverse side effects of the drug as defined by total body weight, which decreased by 40% (FIG. 13C). Moreover, after 20 days the tumors in the group of cisplatin treated mice that survived began to grow, despite continued treatment with cisplatin, and all the remaining mice died within 10 days (FIG. 13A).

Figure 13D:
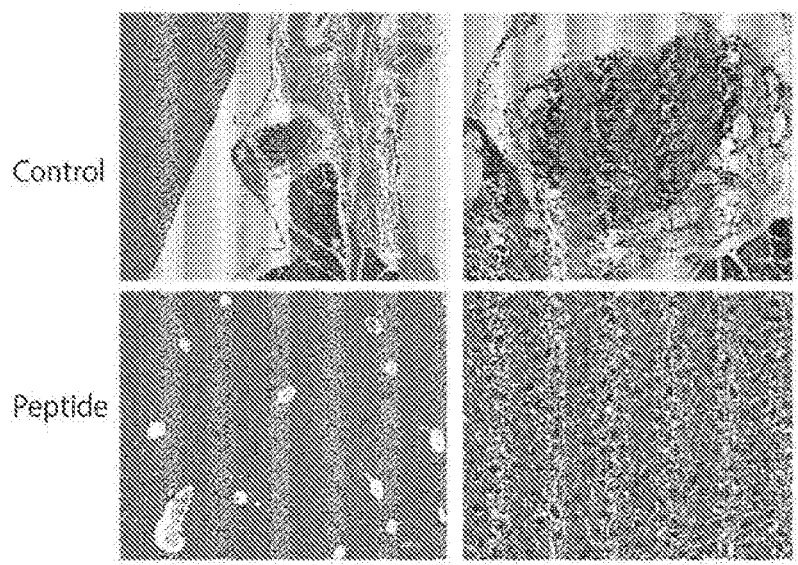
Figure 13E:
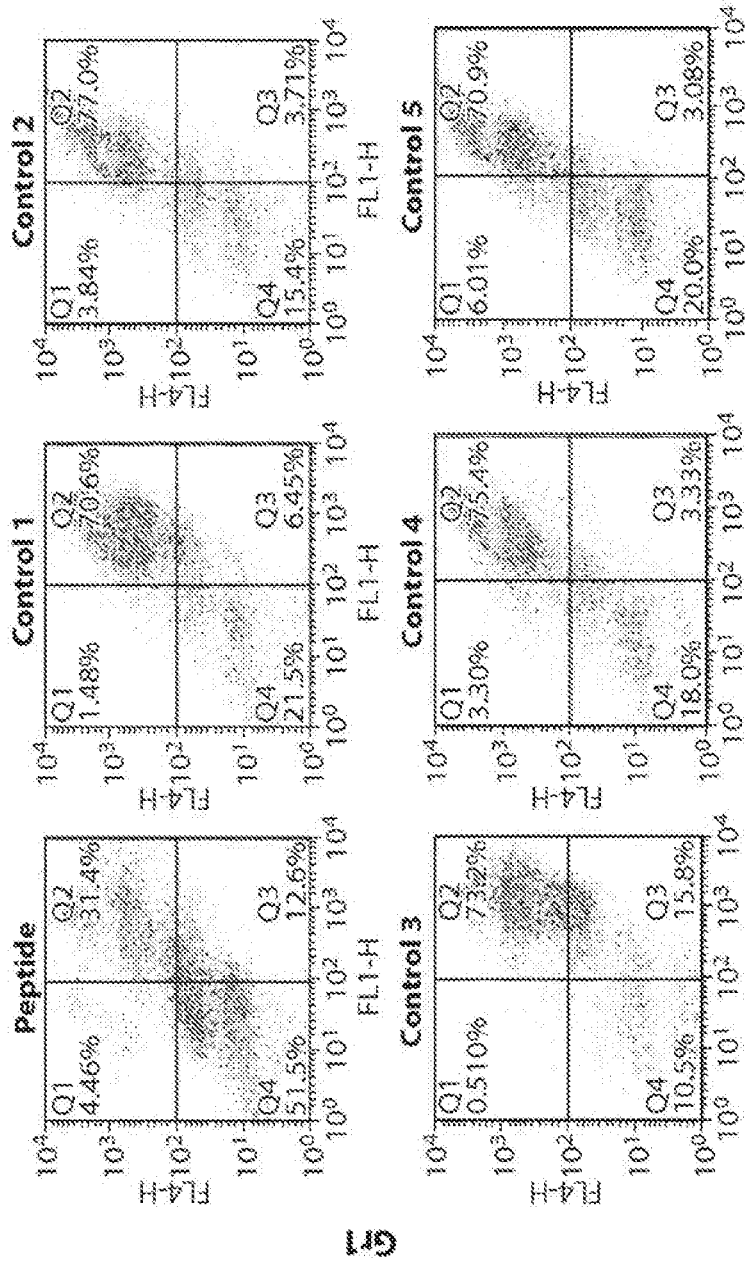
Figure 16:
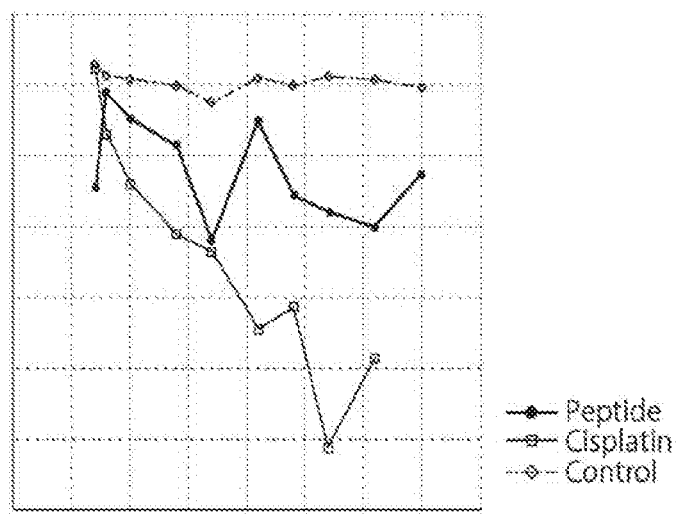
FIG. 16 shows that the psap peptide had no effect on body weight.
Figure 17:
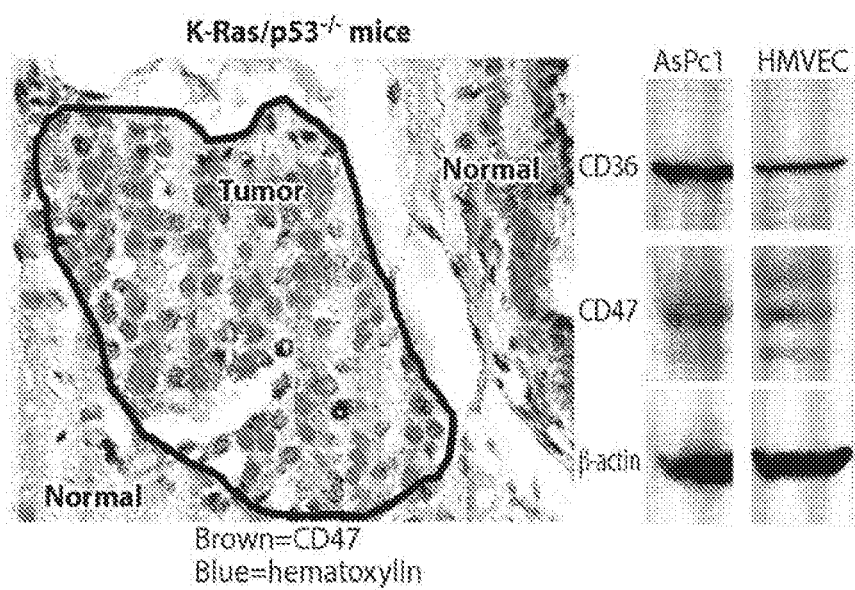
FIG. 17 shows pancreatic cancer cells expressing Tsp-1 receptors.
Figure 18:
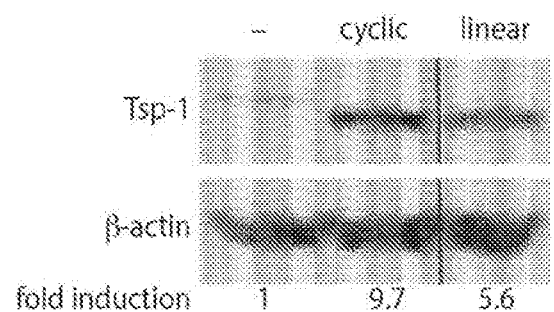
FIG. 18 shows that a cyclic prosaposin peptide DWLPK (SEQ ID NO: 1) has approximately 2-fold great activity than the linear peptide.
Figure 19:
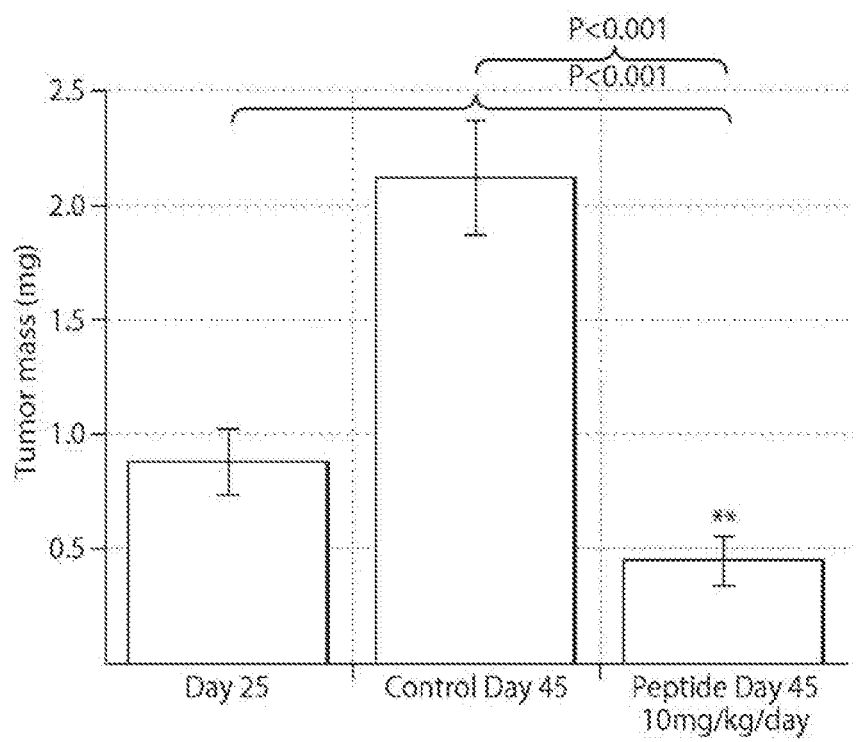
FIG. 19 shows that a cyclic prosaposin peptide DWLPK (SEQ ID NO: 1) has significant anti-tumor activity against pancreatic cancer.
Figure 20:
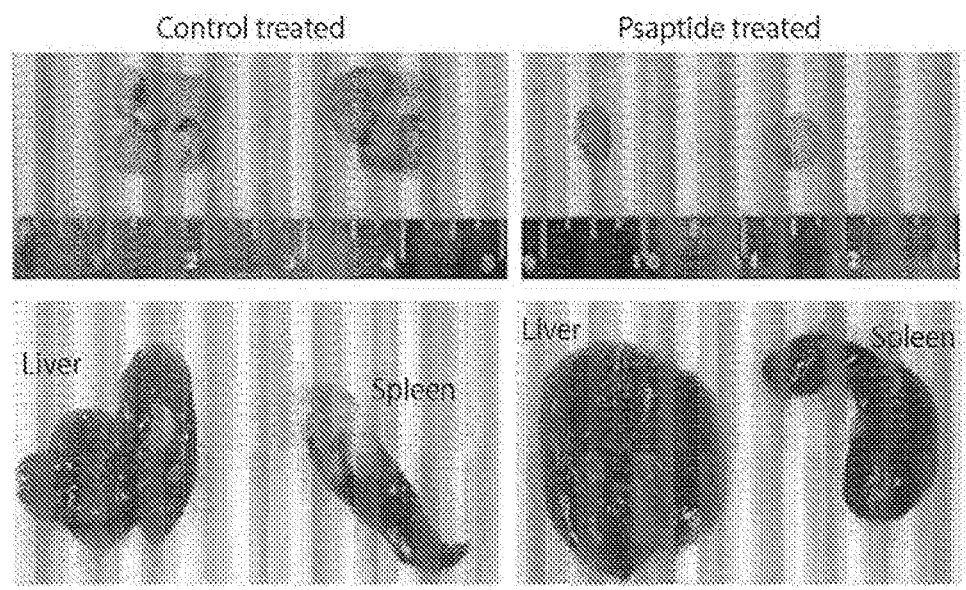
FIG. 20 shows cyclic Psap peptide DWLPK (SEQ ID NO: 1) regresses metastatic pancreatic cancer and inhibits metastasis.

Conversely, no loss of body weight was observed in the group of peptide treated mice (FIG. 13C) and the tumors continued to shrink until by day 48 there was no detectable luciferase signal in any of the mice (FIGS. 13A and 13B and FIG. 16). These mice were treated for an additional 35 days (83 days in total) until the control treated group displayed conditions associated with morbidity. During this treatment time the luciferase signal never re-emerged and gross examination of the mice revealed no metastatic lesions (FIGS. 13A and 13D). The livers and spleens of the Psap peptide treated mice were examined histologically (H&E) to determine whether there were any micrometastases. Metastatic lesions in the Psap peptide treated mice were not identifiable (FIG. 13E).

Metastases in the peritoneal cavity recruited Cd11b'/Gr1' bone marrow derived cells, analogous to lung metastases was investigated (3). Ascites fluid were collected from the peritoneal cavity of control treated mice bearing DF14 metastases and fluid from the peritoneal cavity of Psap peptide treated mice that showed no signs of metastases. The fluid was FACS sorted from these mice to assess the population of $Cd11b^+/Gr1^+$ bone marrow derived cells. The FACS analysis revealed that 71-77% of the cells in the peritoneal fluid of control treated mice were $Cd11b^+/Gr1^+$ (FIG. 13E and FIG. 16) while only 31.4% of the cells in the peritoneal fluid from peptide treated mice were $Cd11b^+/Gr1^+$ (FIG. 13E). Based on these findings it was concluded that the Psap peptide was able to dramatically regress established metastases to the point where no detectable lesions could be found.

Cyclization Further Stabilizes the Psap Peptide while Increasing its Activity

Figure 14A:
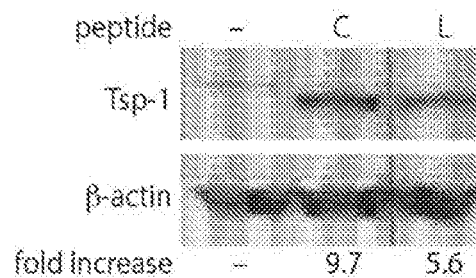
FIGS. 14A-14F show the effects of a cyclic prosaposin peptide on Tsp-1 expression and a PDX model of metastatic ovarian cancer.
Figure 14B:
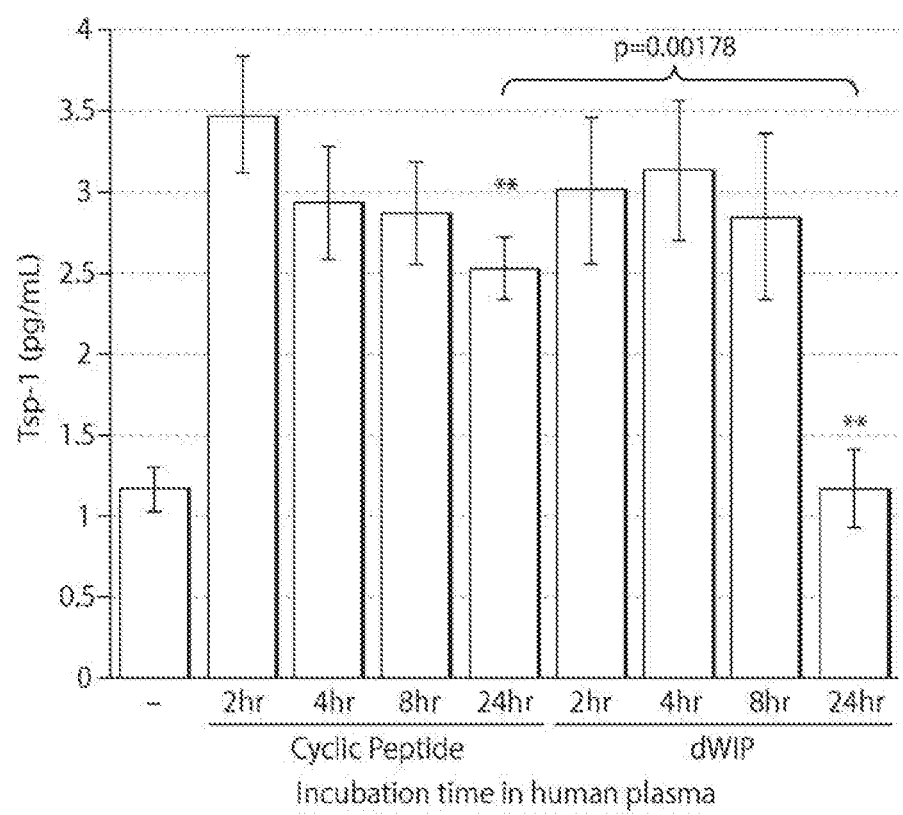

While the results of the peptide treatment of the PDX model of ovarian cancer were very promising it was postulated that the stability and activity of the peptide could be increased even more. The peptide derived from Psap was located in a region of the protein that contained a 13-amino acid loop between two helices that was stabilized by a disulfide bond (3). As such a 5-amino acid peptide that was cyclized via backbone (N—C) cyclization was synthesized (FIG. 14A, cyclic DWLPK (SEQ ID NO: 1)). The activity of this peptide in vitro was tested based on its ability to stimulate Tsp-1. The cyclic peptide stimulated Tsp-1 3-fold greater than the d-amino acid linear peptide (FIG. 14B).

Figure 14C:
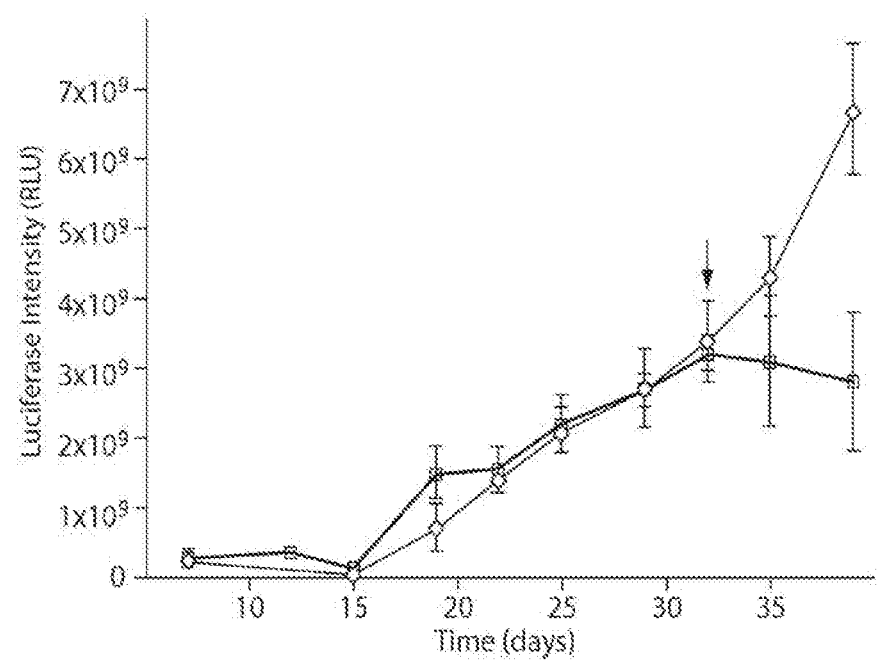

Cyclization also has the effect of increasing the stability of peptides by forcing them into a conformation that is not recognized by most naturally occurring proteases (9, 10, 14-18). The stability of the cyclic peptide to the linear d-amino acid peptide in human plasma was compared. Both peptides in human plasma were incubated at 37° C. for up to 24 hours and then the ability of the plasma/peptide mixture to stimulate Tsp-1 in WI-38 fibroblasts was tested. The level of secreted Tsp-1 was measured following treatment with the peptide/plasma mixture by ELISA and found that the stimulation of Tsp-1 by the two peptides was roughly equivalent after up to 8 hours of incubation (FIG. 14C). However, after 24 hours of incubation in human plasma, the cyclic peptide retained greater than 70% of its Tsp-1 stimulating activity, while the plasma containing linear peptide was no longer able to stimulate Tsp-1 (FIG. 14C). As such, it was concluded that the cyclic peptide was significantly more active and stable than the linear d-amino acid peptide.

Figure 14D:
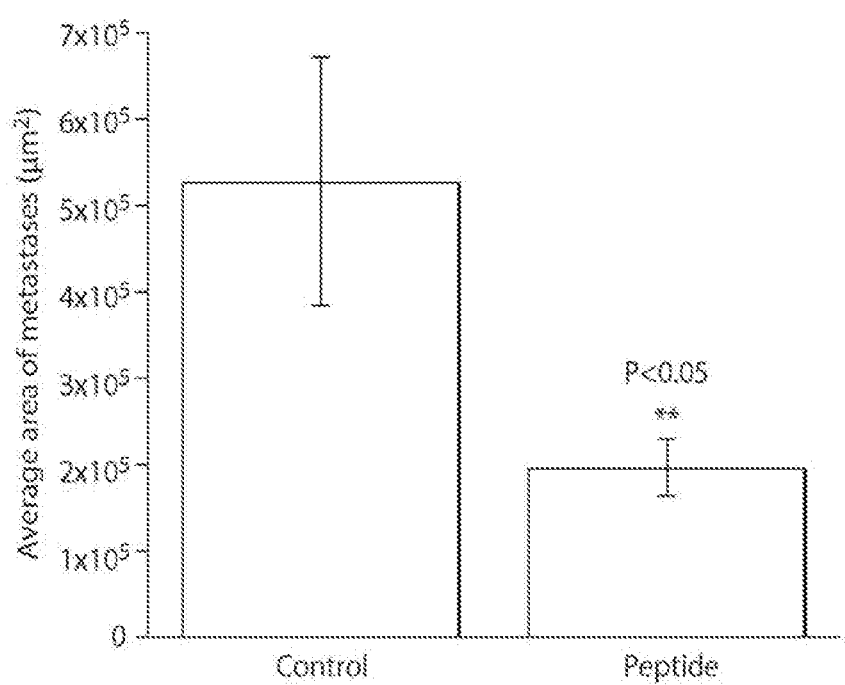
Figure 14E:
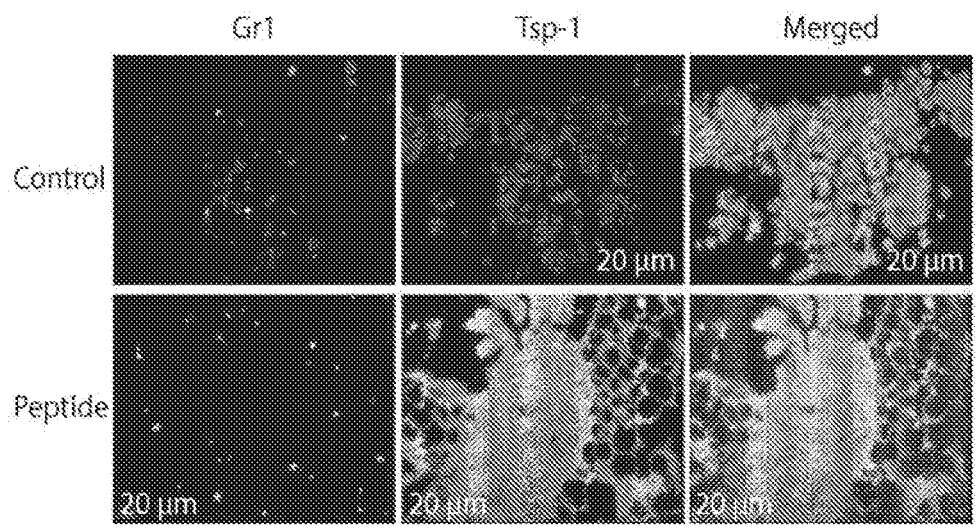
Figure 14F:
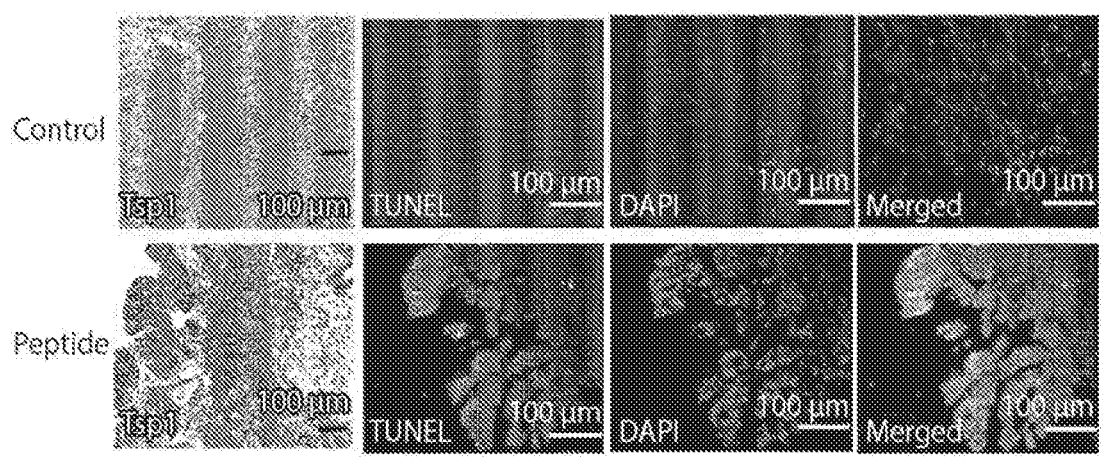

Based on these findings the efficacy of the cyclic peptide using the DF14 model was tested. In order to better study the effects of the peptide on the metastatic lesions mice were injected with $1 \times 10^7$ cells and allowed the luciferase signal to reach $9 \times 10^9$ RLU. The mice were treated with the cyclic peptide for only 10 days to ensure that there would be sufficient tumor tissue to analyze. Significantly, after only 10 days of treatment, the average luciferase signal in the peptide treated mice decreased to $4 \times 10^8$ (FIG. 14D). The liver, spleen and omentum were analyzed of both the peptide and control treated mice by H&E, and IHC for Tsp-1, Gr1 and TUNEL. The metastatic lesions in the control treated mice were, on average, 2,3-fold larger than those in the peptide treated mice (FIG. 14E). Consistent with the mechanism of action (MOA) of the Psap peptide, all of the peptide treated tumors stained positive for Tsp-1 (FIG. 14F) expression. Also consistent with previous observations, it was found that all of the Tsp-1 expressing cells were also Gr1 positive (FIG. 14G) (3). Moreover, all of the lesions in the peptide treated mice contained a significant percentage of TUNEL positive cells, with an average of 40% TUNEL positive cells/lesion (FIGS. 14H and 14I). Conversely, control treated tumors contained, on average, only 1.4% TUNEL positive cells/lesion (FIGS. 14H and 14I).

Metastatic Serous Ovarian Tumors Express Lower Levels of Psap but Higher CD36 Expression than Primary Tumors It was previously demonstrated that the activity of the Psap peptides against tumors formed by patient derived ovarian cancer cells expressed CD36. The prevalence of CD36 expression in human ovarian cancer patients, and thus how widely applicable a potential Psap-based therapeutic agent would be for this disease was investigated. It was postulated that prosaposin expression should decrease as tumors progress to the metastatic stage. Accordingly, a tumor tissue microarray (TMA) comprised of 139 patients with metastatic serous ovarian cancer and normal ovarian tissue from 46 patients was utilized. The tissue for CD36 and Psap expression was stained and then scored the intensity using the staining index (SI) method (R. Catena et al., Bone marrow-derived Gr1+ cells can generate a metastasis-resistant microenvironment via induced secretion of thrombospondin-1, Cancer Discov 3, 578-589 (2013)). 61% of tissue from normal ovaries expressed CD36 with an average SI of 2.39 (out of a possible maximum score of 9) (FIGS. 15A-15C, 15M and Table 1). Analysis of 134 primary ovarian tumors revealed that 97% (130/134) of tumors stained positive for CD36 with an average SI of 5.32 (FIGS. 15D-15F, 15M and Table 1). 121 visceral metastases from the 134 patients were examined. 97% (117/121) of the metastatic lesions stained positive for CD36 with an average SI of 6.61 (FIGS. 15G-15I, 15M and Table 1). Finally, 100% of lymph node metastases (13/13) stained positive for CD36 with an average SI of 6.69 (FIGS. 15J-15L, 15M and Table 1).

TABLE 1

CD36 expression in human ovarian cancer patient TMA

| | Staining Index | % Positive Samples | % Samples > 6 |
|---|---|---|---|
| Normal | 2.39 | 62 | 28.3 |
| Primary Serous EOC | 5.38 | 94 | 79.9 |
| Visceral Metastases | 6.61 | 97 | 91.7 |
| Lymph node metastases | 6.69 | 97 | 92.3 |

Figure 15A:
FIGS. 15A-N show expression of CD36 and prosaposin in a TMA of human ovarian cancer patients.
Figure 15B:
Figure 15C:
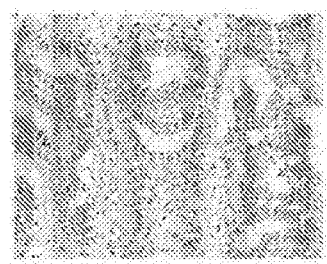
Figure 15D:
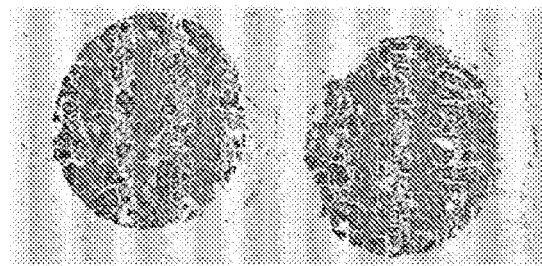
FIGS. 15D-15F show the expression of CD36 in primary human ovarian tumors (Magnification: A=5×, B=10×, C=20×)
Figure 15E:
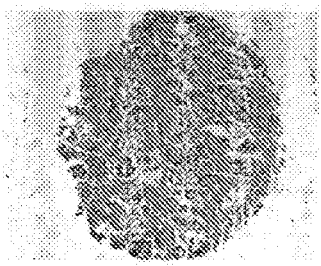
Figure 15F:
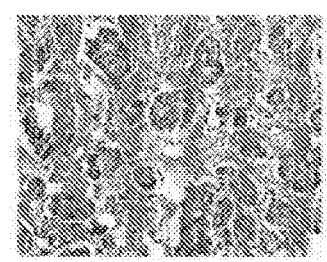
Figure 15G:
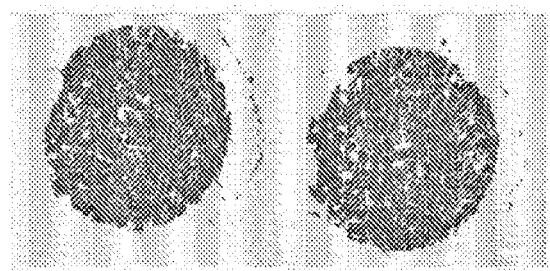
FIGS. 15G-15I show the expression of CD36 in human ovarian cancer metastases (Magnification: A=5×, B=10×, C=20×)
Figure 15H:
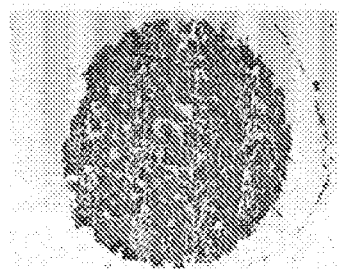
Figure 15I:
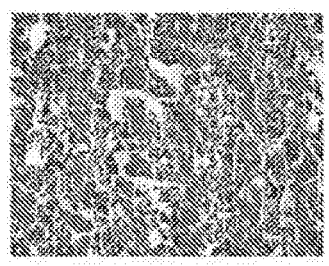
Figure 15J:
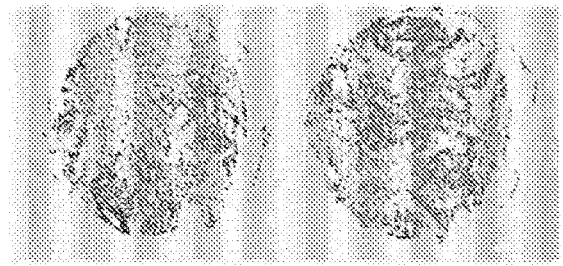
FIGS. 15J-15L show the expression of CD36 in human ovarian cancer lymph node metastases (Magnification: A=5×, B=10×, C=20×)
Figure 15K:
Figure 15L:
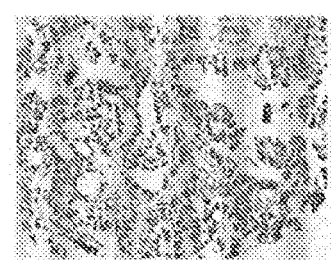
Figure 15M:
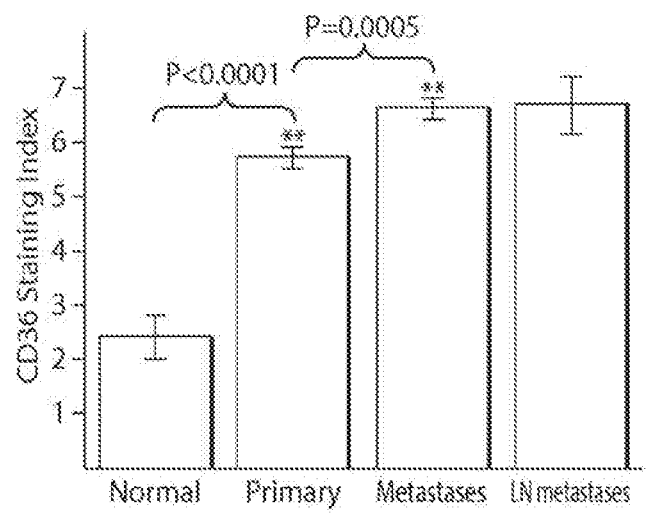
FIG. 15M is a plot of CD36 staining indices of normal human ovaries, primary human ovarian tumors, human ovarian cancer metastases, and human ovarian cancer lymph node metastases.
Figure 15N:
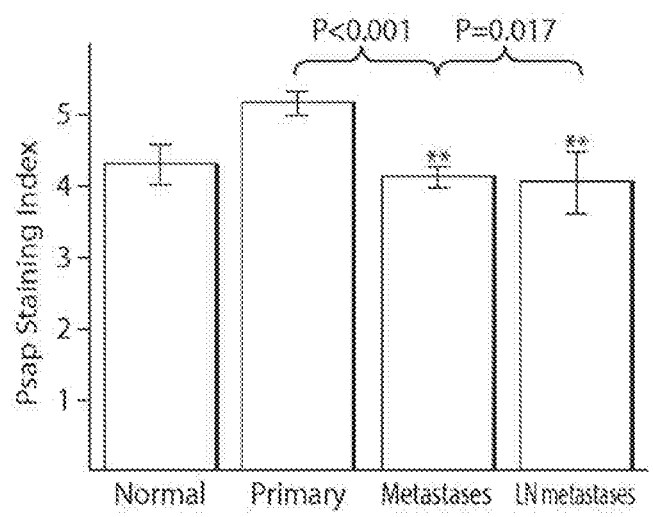

Expression of prosaposin in human ovarian cancer patients was investigated with the speculation that levels should decrease with tumor progression based on its mechanism of action. Prosaposin levels in the ovarian cancer TMA samples were examined. Normal ovaries expressed relatively low levels of prosaposin with an average SI of 4.29 (FIG. 15N and Table 2). Primary ovarian tumors expressed higher levels of prosaposin, with an average SI of 5.17 (FIG. 15N and Table 2). Strikingly, in visceral and lymph node metastases prosaposin levels dropped significantly, with average SI's of 4.14 and 4.07 respectively (FIG. 15N and Table 2). Thus, when taken together, CD36 expression is increased in primary ovarian tumors compared to normal ovaries and that CD36 expression in metastatic lesions is further increased compared to primary tumors, while prosaposin expression decreases with tumor progression. These findings suggest that metastatic ovarian tumors repress prosaposin expression but retain CD36, which could be used to effectively target ovarian cancer with a prosaposin-derived therapy.

TABLE 2

Prosaposin expression in human ovarian cancer patient TMA

| | Psap Staining Index | P-value |
|---|---|---|
| Normal | 4.3 | N/A |
| Primary Serous EOC | 5.17 | N/A |
| Visceral Metastases | 4.14 | <0.001 |
| Lymph node metastases | 4.07 | 0.017 |

Discussion

It was previously demonstrated that prosaposin and a short 5-amino acid peptide derived from it can potently inhibit metastasis (3, 4). The development process of a cyclic peptide derived from prosaposin is delineated with significantly greater activity and stability than the native peptide. It was demonstrated that incorporation of d-amino acids at the first and third residues of the native linear peptide increases in vivo activity. The peptide was further modified to make it more drug-like by cyclizing a 5-amino acid peptide via backbone N—C cyclization. The cyclic peptide displays even greater in vivo activity than the d-amino acid linear peptide. It was demonstrated that both modified peptides can potently regress established metastases in a PDX model of ovarian cancer. The cells used in this PDX model were derived from platinum resistant patients, the most common first line treatment for ovarian cancer patients.

Through an analysis of human ovarian cancer cell lines derived directly from patient ascites it was found that all tested cell lines express CD36, the receptor for Tsp-1, the downstream target of Psap and the peptide in bone marrow derived cells. It was also demonstrated that recombinant Tsp-1 induces apoptosis in these CD36 expressing serous ovarian cancer cells. The in vitro activity of Tsp-1 on ovarian cancer cells was recapitulated in a PDX model of ovarian cancer in which the cyclic Psap peptide stimulated the expression of Tsp-1 in Cd11b+/Gr1+ bone marrow derived cells, which were recruited to the peritoneal cavity of metastasis bearing mice. The induced expression of Tsp-1 in these cells resulted in a significant induction of apoptosis in the tumor cells and significant regression.

Based on these results it is believed that the Psap peptide has the potential to inhibit ovarian cancer progression via three distinct mechanisms, all mediated by the induction of Tsp-1. The first, demonstrated here, is the direct cell killing mediated by downstream signaling from CD36 triggered by Tsp-1. The second is via the widely established anti-angiogenic activity of Tsp-1 (D. J. Good et al., A tumor suppressor-dependent inhibitor of angiogenesis is immunologically and functionally indistinguishable from a fragment of thrombospondin, Proc Natl Acad Sci USA 87, 6624-6628 (1990)). The third is via Tsp-1 binding to its other cell surface receptor, CD47, and blocking the "do not eat me" signal mediated by CD47 binding to SIRPα on macrophages (P. Burger, P. Hilarius-Stokman, D. de Korte, T. K. van den Berg, R. van Bruggen, CD47 functions as a molecular switch for erythrocyte phagocytosis, Blood 119, 5512-5521 (2012); A. Saumet, M. B. Slimane, M. Lanotte, J. Lawler, V. Dubernard, Type 3 repeat/C-terminal domain of thrombospondin-1 triggers caspase-independent cell death through CD47/alphavbeta3 in promyelocytic leukemia NB4 cells, Blood 106, 658-667 (2005)).

Finally, an analysis of tumor tissue from 134 patients with serous ovarian cancer revealed that 97% expressed CD36 and that this expression was not only maintained in metastatic lesions, but that the level of CD36 expression actually increased with tumor progression. The most common first line therapeutic strategy for ovarian cancer patients is platinum-based chemotherapy (E. Lengyel, Ovarian cancer development and metastasis, Am J Pathol 177, 1053-1064 (2010)). 70% of ovarian cancer patients develop resistance to this treatment (E. Lengyel, Ovarian cancer development and metastasis, Am J Pathol 177, 1053-1064 (2010)). For these patients there is no effective FDA approved therapeutic agent and, as such, the survival rate is ~17% (E. Lengyel, Ovarian cancer development and metastasis, Am J Pathol 177, 1053-1064 (2010)). The findings presented here suggest that a Psap-based therapeutic agent could have significant efficacy for the vast majority of ovarian cancer patients based on its mechanism of action and the pervasiveness of CD36 expression in the tumor cells of these patients.

REFERENCES

1. K. Matsuo, V. K. Bond, M. L. Eno, D. D. Im, N. B. Rosenshein, Low drug resistance to both platinum and taxane chemotherapy on an in vitro drug resistance assay predicts improved survival in patients with advanced epithelial ovarian, fallopian and peritoneal cancer, Int J Cancer 125, 2721-2727 (2009).
2. K. Matsuo, M. L. Eno, D. D. Im, N. B. Rosenshein, A. K. Sood, Clinical relevance of extent of extreme drug resistance in epithelial ovarian carcinoma, Gynecol Oncol 116, 61-65 (2010).
3. R. Catena, N. Bhattacharya, T. El Rayes, S. Wang, H. Choi, D. Gao, S. Ryu, N. Joshi, D. Bielenberg, S. B. Lee, S. A. Haukaas, K. Gravdal, O. J. Halvorsen, L. A. Akslen, R. S. Watnick, V. Mittal, Bone marrow-derived Gr1+ cells can generate a metastasis-resistant microenvironment via induced secretion of thrombospondin-1, Cancer discovery 3, 578-589 (2013).
4. S. Y. Kang O. J. Halvorsen, K. Gravdal, N. Bhattacharya, J. M. Lee, N. W. Liu, B. T. Johnston, A. B. Johnston, S. A. Haukaas, K. Aamodt, S. Yoo, L. A. Akslen, R. S. Watnick, Prosaposin inhibits tumor metastasis via paracrine and endocrine stimulation of stromal p53 and Tsp-1, Proc Natl Acad Sci USA 106, 12115-12120 (2009); published online EpubJul 21 (10.1073/pnas.0903120106).
5. D. W. Dawson, S. F. Pearce, R. Zhong, R. L. Silverstein, W. A. Frazier, N. P. Bouck, CD36 mediates the In vitro inhibitory effects of thrombospondin-1 on endothelial cells, Journal of Cell Biology 138, 707-717 (1997).
6. V. Bobde, Y. U. Sasidhar, S. Durani, Harnessing D-amino acids for peptide motif designs, Synthesis and solution conformation of Boc-D-Glu-Ala-Gly-Lys-NHMe and Boc-L-Glu-Ala-Gly-Lys-NHMe, International journal of peptide and protein research 43, 209-218 (1994).
7. M. Coltrera, M. Rosenblatt, J. T. Potts, Jr., Analogues of parathyroid hormone containing D-amino acids: evaluation of biological activity and stability, Biochemistry 19, 4380-4385 (1980).
8. A. S. Dutta, M. B. Giles, Polypeptides, Part XIV, A comparative study of the stability towards enzymes of model tripeptides containing alpha-aza-amino-acids, L-amino-acids, and D-amino-acids, Journal of the Chemical Society, Perkin transactions 1, 244-248 (1976).
9. A. G. Lamont, M. F. Powell, S. M. Colon, C. Miles, H. M. Grey, A. Sette, The use of peptide analogs with improved stability and MHC binding capacity to inhibit antigen presentation in vitro and in vivo, J Immunol 144, 2493-2498 (1990).
10. M. F. Powell, T. Stewart, L. Otvos, Jr., L. Urge, F. C. Gaeta, A. Sette, T. Arrhenius, D. Thomson, K. Soda, S. M. Colon, Peptide stability in drug development, II, Effect of single amino acid substitution and glycosylation on peptide reactivity in human serum. Pharmaceutical research 10, 1268-1273 (1993); published online EpubSep
11. J. Greenaway, J. Henkin, J. Lawler, R. Moorehead, J. Petrik, ABT-510 induces tumor cell apoptosis and inhibits ovarian tumor growth in an orthotopic, syngeneic model of epithelial ovarian cancer, Molecular cancer therapeutics 8, 64-74 (2009); published online EpubJan (10.1158/1535-7163.MCT-08-0864).
12. J. J. Petrik, P. A. Gentry, J. J. Feige, J. LaMarre, Expression and localization of thrombospondin-1 and -2 and their cell-surface receptor, CD36, during rat follicular development and formation of the corpus luteum, Biology of reproduction 67, 1522-1531 (2002).
13. S. Russell, M. Duquette, J. Liu, R. Drapkin, J. Lawler, J. Petrik, Combined therapy with thrombospondin-1 type I repeats (3TSR) and chemotherapy induces regression and significantly improves survival in a preclinical model of advanced stage epithelial ovarian cancer, Faseb J, (2014); published online EpubNov 13 (10.1096/fj.14-261636).
14. S. J. Bogdanowich-Knipp, S. Chakrabarti, T. D. Williams, R. K. Dillman, T. J. Siahaan, Solution stability of linear vs. cyclic RGD peptides. The journal of peptide research: official journal of the American Peptide Society 53, 530-541 (1999).
15. H. Iwai, A. Pluckthun, Circular beta-lactamase: stability enhancement by cyclizing the backbone, FEBS Lett 459, 166-172 (1999); published online EpubOct 8
16. A. X. Ji, M. Bodanszky, Cyclization studies with a model pentapeptide, International journal of peptide and protein research 22, 590-596 (1983).
17. J. Moss, H. Bundgaard, Kinetics and mechanism of the facile cyclization of histidyl-prolinamide to cyclo (His- Pro) in aqueous solution and the competitive influence of human plasma. The Journal of pharmacy and pharmacology 42, 7-12 (1990).
18. J. Samanen, F. Ali, T. Romoff, R. Calvo, E. Sorenson, J. Vasko, B. Storer, D. Berry, D. Bennett, M. Strohsacker, et al., Development of a small RGD peptide fibrinogen receptor antagonist with potent antiaggregatory activity in vitro, Journal of medicinal chemistry 34, 3114-3125 (1991).

Without further elaboration, it is believed that one skilled in the art can, based on the above description, utilize the present disclosure to its fullest extent. The specific embodiments are, therefore, to be construed as merely illustrative, and not limitative of the remainder of the disclosure in any way whatsoever. All publications cited herein are incorporated by reference for the purposes or subject matter referenced herein.

The indefinite articles "a" and "an," as used herein in the specification and in the claims, unless clearly indicated to the contrary, should be understood to mean "at least one."

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

What is claimed is:

1. A method for treating cancer in a subject in need thereof, the method comprising:
   administering to the subject an effective amount of a cyclic peptide with a sequence consisting of DWGPK (SEQ ID NO: 2) or dWGPK (SEQ ID NO:4).

2. The method of claim 1, wherein the cancer is ovarian cancer or melanoma.

3. The method of claim 1, wherein the peptide is linked to a polymer that enhances the serum half-life.

4. The method of claim 3, wherein the polymer is selected from the group consisting of polyvinyl pyrrolidone, polyvinyl alcohol, divinylether, maleic anhydride, N-(2-hydroxypropyl)-methacrylamide, dextran, dextran sulfate, polypropylene glycol, polyoxyethylated polyol, heparin, heparin fragments, polysaccharides, cellulose, methylcellulose, carboxymethyl cellulose, starch, polyalkylene glycol and derivatives thereof, copolymers of polyalkylene glycols and derivatives thereof, polyvinyl ethyl ethers, and α,β-Poly(2-hydroxyethyl)-DL-aspartamide.

* * * * *

SEQUENCE LISTING

```
<160> NUMBER OF SEQ ID NOS: 12

<210> SEQ ID NO 1
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 1

Asp Trp Leu Pro Lys
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 2

Asp Trp Gly Pro Lys
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Asp is a D-amino acid

<400> SEQUENCE: 3

Asp Trp Leu Pro Lys
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Asp is a D-amino acid

<400> SEQUENCE: 4

Asp Trp Gly Pro Lys
1               5
```

```
<210> SEQ ID NO 5
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Asp is a D-amino acid
<220> FEATURE:
<221> NAME/KEY: misc_feature
<222> LOCATION: (3)..(3)
<223> OTHER INFORMATION: Leu is a D-amino acid

<400> SEQUENCE: 5

Asp Trp Leu Pro
1

<210> SEQ ID NO 6
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 6

Asp Trp Leu Pro
1

<210> SEQ ID NO 7
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Trp is a D-amino acid
<220> FEATURE:
<221> NAME/KEY: misc_feature
<222> LOCATION: (4)..(4)
<223> OTHER INFORMATION: Pro is a D-amino acid

<400> SEQUENCE: 7

Asp Trp Leu Pro
1

<210> SEQ ID NO 8
<211> LENGTH: 40
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (6)..(40)
<223> OTHER INFORMATION: these amino acids may be absent

<400> SEQUENCE: 8

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser
        35                  40
```

<210> SEQ ID NO 9
<211> LENGTH: 524
<212> TYPE: PRT
<213> ORGANISM: Artificial Sequence
<220> FEATURE:
<223> OTHER INFORMATION: Synthetic Polypeptide

<400> SEQUENCE: 9

```
Met Tyr Ala Leu Phe Leu Leu Ala Ser Leu Leu Gly Ala Leu Ala
1               5                   10                  15

Gly Pro Val Leu Gly Leu Lys Glu Cys Thr Arg Gly Ser Ala Val Trp
            20                  25                  30

Cys Gln Asn Val Lys Thr Ala Ser Asp Cys Gly Ala Val Lys His Cys
        35                  40                  45

Leu Gln Thr Val Trp Asn Lys Pro Thr Val Lys Ser Leu Pro Cys Asp
    50                  55                  60

Ile Cys Lys Asp Val Val Thr Ala Ala Gly Asp Met Leu Lys Asp Asn
65                  70                  75                  80

Ala Thr Glu Glu Glu Ile Leu Val Tyr Leu Lys Thr Cys Asp Trp
                85                  90                  95

Leu Pro Lys Pro Asn Met Ser Ala Ser Cys Lys Glu Ile Val Asp Ser
            100                 105                 110

Tyr Leu Pro Val Ile Leu Asp Ile Ile Lys Gly Glu Met Ser Arg Pro
        115                 120                 125

Gly Glu Val Cys Ser Ala Leu Asn Leu Cys Glu Ser Leu Gln Lys His
    130                 135                 140

Leu Ala Glu Leu Asn His Gln Lys Gln Leu Glu Ser Asn Lys Ile Pro
145                 150                 155                 160

Glu Leu Asp Met Thr Glu Val Val Ala Pro Phe Met Ala Asn Ile Pro
                165                 170                 175

Leu Leu Leu Tyr Pro Gln Asp Gly Pro Arg Ser Lys Pro Gln Pro Lys
            180                 185                 190

Asp Asn Gly Asp Val Cys Gln Asp Cys Ile Gln Met Val Thr Asp Ile
        195                 200                 205

Gln Thr Ala Val Arg Thr Asn Ser Thr Phe Val Gln Ala Leu Val Glu
    210                 215                 220

His Val Lys Glu Glu Cys Asp Arg Leu Gly Pro Gly Met Ala Asp Ile
225                 230                 235                 240

Cys Lys Asn Tyr Ile Ser Gln Tyr Ser Glu Ile Ala Ile Gln Met Met
                245                 250                 255

Met His Met Gln Pro Lys Glu Ile Cys Ala Leu Val Gly Phe Cys Asp
            260                 265                 270

Glu Val Lys Glu Met Pro Met Gln Thr Leu Val Pro Ala Lys Val Ala
        275                 280                 285

Ser Lys Asn Val Ile Pro Ala Leu Glu Leu Val Glu Pro Ile Lys Lys
    290                 295                 300

His Glu Val Pro Ala Lys Ser Asp Val Tyr Cys Glu Val Cys Glu Phe
305                 310                 315                 320

Leu Val Lys Glu Val Thr Lys Leu Ile Asp Asn Asn Lys Thr Glu Lys
                325                 330                 335

Glu Ile Leu Asp Ala Phe Asp Lys Met Cys Ser Lys Leu Pro Lys Ser
            340                 345                 350

Leu Ser Glu Glu Cys Gln Glu Val Val Asp Thr Tyr Gly Ser Ser Ile
        355                 360                 365

Leu Ser Ile Leu Leu Glu Glu Val Ser Pro Glu Leu Val Cys Ser Met
```

```
                370                 375                 380
Leu His Leu Cys Ser Gly Thr Arg Leu Pro Ala Leu Thr Val His Val
385                 390                 395                 400

Thr Gln Pro Lys Asp Gly Gly Phe Cys Glu Val Cys Lys Lys Leu Val
                405                 410                 415

Gly Tyr Leu Asp Arg Asn Leu Glu Lys Asn Ser Thr Lys Gln Glu Ile
                420                 425                 430

Leu Ala Ala Leu Glu Lys Gly Cys Ser Phe Leu Pro Asp Pro Tyr Gln
            435                 440                 445

Lys Gln Cys Asp Gln Phe Val Ala Glu Tyr Glu Pro Val Leu Ile Glu
        450                 455                 460

Ile Leu Val Glu Val Met Asp Pro Ser Phe Val Cys Leu Lys Ile Gly
465                 470                 475                 480

Ala Cys Pro Ser Ala His Lys Pro Leu Leu Gly Thr Glu Lys Cys Ile
                485                 490                 495

Trp Gly Pro Ser Tyr Trp Cys Gln Asn Thr Glu Thr Ala Ala Gln Cys
                500                 505                 510

Asn Ala Val Glu His Cys Lys Arg His Val Trp Asn
            515                 520

<210> SEQ ID NO 10
<211> LENGTH: 527
<212> TYPE: PRT
<213> ORGANISM: Artificial Sequence
<220> FEATURE:
<223> OTHER INFORMATION: Synthetic Polypeptide

<400> SEQUENCE: 10

Met Tyr Ala Leu Phe Leu Leu Ala Ser Leu Leu Gly Ala Ala Leu Ala
1               5                   10                  15

Gly Pro Val Leu Gly Leu Lys Glu Cys Thr Arg Gly Ser Ala Val Trp
                20                  25                  30

Cys Gln Asn Val Lys Thr Ala Ser Asp Cys Gly Ala Val Lys His Cys
            35                  40                  45

Leu Gln Thr Val Trp Asn Lys Pro Thr Val Lys Ser Leu Pro Cys Asp
50                  55                  60

Ile Cys Lys Asp Val Val Thr Ala Ala Gly Asp Met Leu Lys Asp Asn
65                  70                  75                  80

Ala Thr Glu Glu Glu Ile Leu Val Tyr Leu Glu Lys Thr Cys Asp Trp
                85                  90                  95

Leu Pro Lys Pro Asn Met Ser Ala Ser Cys Lys Glu Ile Val Asp Ser
                100                 105                 110

Tyr Leu Pro Val Ile Leu Asp Ile Ile Lys Gly Glu Met Ser Arg Pro
            115                 120                 125

Gly Glu Val Cys Ser Ala Leu Asn Leu Cys Glu Ser Leu Gln Lys His
        130                 135                 140

Leu Ala Glu Leu Asn His Gln Lys Gln Leu Glu Ser Asn Lys Ile Pro
145                 150                 155                 160

Glu Leu Asp Met Thr Glu Val Val Ala Pro Phe Met Ala Asn Ile Pro
                165                 170                 175

Leu Leu Leu Tyr Pro Gln Asp Gly Pro Arg Ser Lys Pro Gln Pro Lys
                180                 185                 190

Asp Asn Gly Asp Val Cys Gln Asp Cys Ile Gln Met Val Thr Asp Ile
            195                 200                 205

Gln Thr Ala Val Arg Thr Asn Ser Thr Phe Val Gln Ala Leu Val Glu
```

```
            210                 215                 220
His Val Lys Glu Glu Cys Asp Arg Leu Gly Pro Gly Met Ala Asp Ile
225                 230                 235                 240

Cys Lys Asn Tyr Ile Ser Gln Tyr Ser Glu Ile Ala Ile Gln Met Met
                245                 250                 255

Met His Met Gln Asp Gln Pro Lys Glu Ile Cys Ala Leu Val Gly
            260                 265                 270

Phe Cys Asp Glu Val Lys Glu Met Pro Met Gln Thr Leu Val Pro Ala
                275                 280                 285

Lys Val Ala Ser Lys Asn Val Ile Pro Ala Leu Glu Leu Val Glu Pro
            290                 295                 300

Ile Lys Lys His Glu Val Pro Ala Lys Ser Asp Val Tyr Cys Glu Val
305                 310                 315                 320

Cys Glu Phe Leu Val Lys Glu Val Thr Lys Leu Ile Asp Asn Asn Lys
                325                 330                 335

Thr Glu Lys Glu Ile Leu Asp Ala Phe Asp Lys Met Cys Ser Lys Leu
            340                 345                 350

Pro Lys Ser Leu Ser Glu Glu Cys Gln Glu Val Val Asp Thr Tyr Gly
            355                 360                 365

Ser Ser Ile Leu Ser Ile Leu Leu Glu Glu Val Ser Pro Glu Leu Val
            370                 375                 380

Cys Ser Met Leu His Leu Cys Ser Gly Thr Arg Leu Pro Ala Leu Thr
385                 390                 395                 400

Val His Val Thr Gln Pro Lys Asp Gly Gly Phe Cys Glu Val Cys Lys
                405                 410                 415

Lys Leu Val Gly Tyr Leu Asp Arg Asn Leu Glu Lys Asn Ser Thr Lys
            420                 425                 430

Gln Glu Ile Leu Ala Ala Leu Glu Lys Gly Cys Ser Phe Leu Pro Asp
            435                 440                 445

Pro Tyr Gln Lys Gln Cys Asp Gln Phe Val Ala Glu Tyr Glu Pro Val
            450                 455                 460

Leu Ile Glu Ile Leu Val Glu Val Met Asp Pro Ser Phe Val Cys Leu
465                 470                 475                 480

Lys Ile Gly Ala Cys Pro Ser Ala His Lys Pro Leu Leu Gly Thr Glu
                485                 490                 495

Lys Cys Ile Trp Gly Pro Ser Tyr Trp Cys Gln Asn Thr Glu Thr Ala
                500                 505                 510

Ala Gln Cys Asn Ala Val Glu His Cys Lys Arg His Val Trp Asn
            515                 520                 525
```

<210> SEQ ID NO 11
<211> LENGTH: 526
<212> TYPE: PRT
<213> ORGANISM: Artificial Sequence
<220> FEATURE:
<223> OTHER INFORMATION: Synthetic Polypeptide

<400> SEQUENCE: 11

```
Met Tyr Ala Leu Phe Leu Leu Ala Ser Leu Leu Gly Ala Ala Leu Ala
1               5                   10                  15

Gly Pro Val Leu Gly Leu Lys Glu Cys Thr Arg Gly Ser Ala Val Trp
            20                  25                  30

Cys Gln Asn Val Lys Thr Ala Ser Asp Cys Gly Ala Val Lys His Cys
            35                  40                  45

Leu Gln Thr Val Trp Asn Lys Pro Thr Val Lys Ser Leu Pro Cys Asp
```

```
                50                  55                  60
Ile Cys Lys Asp Val Val Thr Ala Ala Gly Asp Met Leu Lys Asp Asn
 65                  70                  75                  80

Ala Thr Glu Glu Ile Leu Val Tyr Leu Glu Lys Thr Cys Asp Trp
                 85                  90                  95

Leu Pro Lys Pro Asn Met Ser Ala Ser Cys Lys Glu Ile Val Asp Ser
                100                 105                 110

Tyr Leu Pro Val Ile Leu Asp Ile Ile Lys Gly Glu Met Ser Arg Pro
                115                 120                 125

Gly Glu Val Cys Ser Ala Leu Asn Leu Cys Glu Ser Leu Gln Lys His
                130                 135                 140

Leu Ala Glu Leu Asn His Gln Lys Gln Leu Glu Ser Asn Lys Ile Pro
145                 150                 155                 160

Glu Leu Asp Met Thr Glu Val Val Ala Pro Phe Met Ala Asn Ile Pro
                165                 170                 175

Leu Leu Leu Tyr Pro Gln Asp Gly Pro Arg Ser Lys Pro Gln Pro Lys
                180                 185                 190

Asp Asn Gly Asp Val Cys Gln Asp Cys Ile Gln Met Val Thr Asp Ile
                195                 200                 205

Gln Thr Ala Val Arg Thr Asn Ser Thr Phe Val Gln Ala Leu Val Glu
                210                 215                 220

His Val Lys Glu Glu Cys Asp Arg Leu Gly Pro Gly Met Ala Asp Ile
225                 230                 235                 240

Cys Lys Asn Tyr Ile Ser Gln Tyr Ser Glu Ile Ala Ile Gln Met Met
                245                 250                 255

Met His Met Asp Gln Gln Pro Lys Glu Ile Cys Ala Leu Val Gly Phe
                260                 265                 270

Cys Asp Glu Val Lys Glu Met Pro Met Gln Thr Leu Val Pro Ala Lys
                275                 280                 285

Val Ala Ser Lys Asn Val Ile Pro Ala Leu Glu Leu Val Glu Pro Ile
                290                 295                 300

Lys Lys His Glu Val Pro Ala Lys Ser Asp Val Tyr Cys Glu Val Cys
305                 310                 315                 320

Glu Phe Leu Val Lys Glu Val Thr Lys Leu Ile Asp Asn Asn Lys Thr
                325                 330                 335

Glu Lys Glu Ile Leu Asp Ala Phe Asp Lys Met Cys Ser Lys Leu Pro
                340                 345                 350

Lys Ser Leu Ser Glu Glu Cys Gln Glu Val Val Asp Thr Tyr Gly Ser
                355                 360                 365

Ser Ile Leu Ser Ile Leu Leu Glu Glu Val Ser Pro Glu Leu Val Cys
370                 375                 380

Ser Met Leu His Leu Cys Ser Gly Thr Arg Leu Pro Ala Leu Thr Val
385                 390                 395                 400

His Val Thr Gln Pro Lys Asp Gly Gly Phe Cys Glu Val Cys Lys Lys
                405                 410                 415

Leu Val Gly Tyr Leu Asp Arg Asn Leu Glu Lys Asn Ser Thr Lys Gln
                420                 425                 430

Glu Ile Leu Ala Ala Leu Glu Lys Gly Cys Ser Phe Leu Pro Asp Pro
                435                 440                 445

Tyr Gln Lys Gln Cys Asp Gln Phe Val Ala Glu Tyr Glu Pro Val Leu
                450                 455                 460

Ile Glu Ile Leu Val Glu Val Met Asp Pro Ser Phe Val Cys Leu Lys
465                 470                 475                 480
```

```
Ile Gly Ala Cys Pro Ser Ala His Lys Pro Leu Leu Gly Thr Glu Lys
            485                 490                 495

Cys Ile Trp Gly Pro Ser Tyr Trp Cys Gln Asn Thr Glu Thr Ala Ala
            500                 505                 510

Gln Cys Asn Ala Val Glu His Cys Lys Arg His Val Trp Asn
            515                 520                 525

<210> SEQ ID NO 12
<211> LENGTH: 81
<212> TYPE: PRT
<213> ORGANISM: Artificial Sequence
<220> FEATURE:
<223> OTHER INFORMATION: Synthetic Polypeptide

<400> SEQUENCE: 12

Ser Leu Pro Cys Asp Ile Cys Lys Asp Val Val Thr Ala Ala Gly Asp
1               5                   10                  15

Met Leu Lys Asp Asn Ala Thr Glu Glu Ile Leu Val Tyr Leu Glu
            20                  25                  30

Lys Thr Cys Asp Trp Leu Pro Lys Pro Asn Met Ser Ala Ser Cys Lys
            35                  40                  45

Glu Ile Val Asp Ser Tyr Leu Pro Val Ile Leu Asp Ile Ile Lys Gly
    50                  55                  60

Glu Met Ser Arg Pro Gly Glu Val Cys Ser Ala Leu Asn Leu Cys Glu
65                  70                  75                  80

Ser
```